US010953170B2

(12) United States Patent
Deem et al.

(10) Patent No.: US 10,953,170 B2
(45) Date of Patent: *Mar. 23, 2021

(54) APPARATUS FOR TREATING ASTHMA USING NEUROTOXIN

(71) Applicant: Nuvaira, Inc., Plymouth, MN (US)

(72) Inventors: Mark E. Deem, Mountain View, CA (US); Hanson S. Gifford, III, Woodside, CA (US)

(73) Assignee: Nuvaira, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,172

(22) Filed: Oct. 9, 2017

(65) Prior Publication Data

US 2018/0028748 A1 Feb. 1, 2018

Related U.S. Application Data

(60) Division of application No. 15/155,641, filed on May 16, 2016, now abandoned, which is a continuation of
(Continued)

(51) Int. Cl.
*A61M 16/00* (2006.01)
*A61M 25/10* (2013.01)
(Continued)

(52) U.S. Cl.
CPC .......... *A61M 16/00* (2013.01); *A61B 1/2676* (2013.01); *A61M 5/30* (2013.01); *A61M 11/00* (2013.01);
(Continued)

(58) Field of Classification Search
CPC ...... A61M 16/00; A61M 16/18; A61M 11/00; A61M 11/06; A61M 5/14276; A61M 5/30;
(Continued)

(56) References Cited

U.S. PATENT DOCUMENTS 612,724 A 10/1898 Hamilton
1,155,169 A 9/1915 John
(Continued)

FOREIGN PATENT DOCUMENTS

CA 2419228 A1 8/2004
CN 101115448 A 1/2008
(Continued)

OTHER PUBLICATIONS

Abbott., "Present Concepts Relative to Autonomic Nerve Surgery in the Treatment of Pulmonary Disease," American Journal of Surgery, 1955, vol. 90, pp. 479-489.
(Continued)

*Primary Examiner* — Colin W Stuart
(74) *Attorney, Agent, or Firm* — Patterson Thuente Pedersen, P.A.

(57) ABSTRACT

Apparatus and methods for providing intrabronchial delivery of a treatment fluid to control the effects of a bronchial condition. The apparatus can include a shaft having proximal and distal ends and a fluid injection assembly disposed on the distal end. The fluid injection assembly can be a deployable needle assembly, a rotating needle assembly, a needle-less injection assembly, or a nebulizer assembly.

8 Claims, 6 Drawing Sheets

Related U.S. Application Data application No. 13/669,305, filed on Nov. 5, 2012, now Pat. No. 9,339,618, which is a continuation of application No. 11/446,043, filed on Jun. 1, 2006, now abandoned, which is a continuation of application No. 10/437,882, filed on May 13, 2003, now abandoned.

(51) Int. Cl.
  *A61M 11/00* (2006.01)
  *A61M 5/30* (2006.01)
  *A61B 1/267* (2006.01)
  *A61M 25/00* (2006.01)
  *A61B 1/018* (2006.01)
  *A61B 1/04* (2006.01)
  *A61B 1/06* (2006.01)
  *A61M 5/145* (2006.01)
  *A61M 5/162* (2006.01)

(52) U.S. Cl.
  CPC .............. *A61M 25/10* (2013.01); *A61B 1/018* (2013.01); *A61B 1/04* (2013.01); *A61B 1/0661* (2013.01); *A61M 5/1452* (2013.01); *A61M 5/162* (2013.01); *A61M 25/0084* (2013.01); *A61M 2025/0086* (2013.01); *A61M 2025/105* (2013.01); *A61M 2202/049* (2013.01); *A61M 2210/1035* (2013.01)

(58) Field of Classification Search
  CPC ............ A61M 5/2053; A61M 39/0208; A61M 39/0247; A61M 25/00; A61M 25/1002; A61M 25/104; A61M 2025/105; A61M 2025/1052; A61M 5/142; A61M 5/1452; A61M 25/10; A61M 25/0082; A61M 25/0074; A61M 2025/0057; A61M 2025/022; A61M 2025/026; A61M 2025/1043; A61M 2025/1065; A61M 2202/049; A61M 2210/1032; A61M 2210/1035; A61B 17/12136; A61B 1/2676; A61B 5/6853; A61B 2017/22051; A61B 2017/22054; A61B 2017/22055; A61B 2017/22065; A61B 2018/0022; A61B 2018/0025; A61B 2018/00285
  See application file for complete search history.

(56) References Cited

U.S. PATENT DOCUMENTS

| | | |
|---|---|---|
| 1,216,183 A | 2/1917 | Charles |
| 1,695,107 A | 12/1928 | Kahl |
| 2,072,346 A | 3/1937 | Smith |
| 2,279,714 A | 4/1942 | Meyerhof et al. |
| 3,320,957 A | 5/1967 | Sokolik |
| 3,568,659 A | 3/1971 | James |
| 3,667,476 A | 6/1972 | Henry |
| 3,692,029 A | 9/1972 | Edwin |
| 3,918,449 A | 11/1975 | Pistor |
| 3,946,745 A | 3/1976 | Hsiang-Lai et al. |
| 3,949,743 A | 4/1976 | Shanbrom |
| 3,995,617 A | 12/1976 | Watkins et al. |
| 4,078,864 A | 3/1978 | Howell |
| 4,095,602 A | 6/1978 | Leveen |
| 4,116,589 A | 9/1978 | Rishton |
| 4,129,129 A | 12/1978 | Amrine |
| 4,154,246 A | 5/1979 | Leveen |
| 4,277,168 A | 7/1981 | Oku |
| 4,305,402 A | 12/1981 | Katims |
| 4,351,330 A | 9/1982 | Scarberry |
| 4,461,283 A | 7/1984 | Doi |
| 4,502,490 A | 3/1985 | Evans et al. |
| 4,503,855 A | 3/1985 | Maslanka |
| 4,503,863 A | 3/1985 | Katims |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,573,481 A | 3/1986 | Bullara |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,649,924 A | 3/1987 | Taccardi |
| 4,649,935 A | 3/1987 | Charmillot et al. |
| 4,658,836 A | 4/1987 | Turner |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,322 A | 8/1988 | Charmillot et al. |
| 4,765,959 A | 8/1988 | Fukasawa |
| 4,767,402 A | 8/1988 | Kost et al. |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,808,164 A | 2/1989 | Hess |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,881,542 A | 11/1989 | Schmidt et al. |
| 4,895,557 A | 1/1990 | Moise et al. |
| 4,902,129 A | 2/1990 | Siegmund et al. |
| 4,904,472 A | 2/1990 | Belardinelli et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,945,910 A | 8/1990 | Budyko et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,976,710 A | 12/1990 | Mackin |
| 4,985,014 A | 1/1991 | Orejola |
| 4,989,604 A | 2/1991 | Fang |
| 4,991,603 A | 2/1991 | Cohen et al. |
| 4,992,474 A | 2/1991 | Skidmore et al. |
| 5,005,559 A | 4/1991 | Blanco et al. |
| 5,007,908 A | 4/1991 | Rydell |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,054,486 A | 10/1991 | Yamada |
| 5,056,519 A | 10/1991 | Vince |
| 5,056,529 A | 10/1991 | De Groot |
| 5,057,107 A | 10/1991 | Parins et al. |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |

(56) References Cited

U.S. PATENT DOCUMENTS

| | | |
|---|---|---|
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,107,835 A | 4/1992 | Thomas |
| 5,109,846 A | 5/1992 | Thomas |
| 5,114,423 A | 5/1992 | Kasprzyk et al. |
| 5,116,864 A | 5/1992 | March et al. |
| 5,117,828 A | 6/1992 | Metzger et al. |
| 5,123,413 A | 6/1992 | Hasegawa et al. |
| 5,126,375 A | 6/1992 | Skidmore et al. |
| 5,135,480 A | 8/1992 | Bannon et al. |
| 5,135,517 A | 8/1992 | McCoy |
| 5,139,029 A | 8/1992 | Fishman et al. |
| 5,151,100 A | 9/1992 | Abele et al. |
| 5,152,286 A | 10/1992 | Sitko et al. |
| 5,158,536 A | 10/1992 | Sekins et al. |
| 5,165,420 A | 11/1992 | Strickland |
| 5,167,223 A | 12/1992 | Koros et al. |
| 5,170,802 A | 12/1992 | Mehra |
| 5,170,803 A | 12/1992 | Hewson et al. |
| 5,174,288 A | 12/1992 | Bardy et al. |
| 5,188,602 A | 2/1993 | Nichols |
| 5,188,632 A | 2/1993 | Goldenberg |
| 5,190,540 A | 3/1993 | Lee |
| 5,191,883 A | 3/1993 | Lennox et al. |
| 5,213,576 A | 5/1993 | Abiuso et al. |
| 5,215,103 A | 6/1993 | Desai |
| 5,224,491 A | 7/1993 | Mehra |
| 5,225,445 A | 7/1993 | Skidmore et al. |
| 5,231,996 A | 8/1993 | Bardy et al. |
| 5,232,444 A | 8/1993 | Just et al. |
| 5,234,456 A | 8/1993 | Silvestrini |
| 5,239,982 A | 8/1993 | Trauthen |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,286,254 A | 2/1994 | Shapland et al. |
| 5,292,331 A | 3/1994 | Boneau |
| 5,293,869 A | 3/1994 | Edwards et al. |
| 5,304,120 A | 4/1994 | Crandell et al. |
| 5,309,910 A | 5/1994 | Edwards et al. |
| 5,311,866 A | 5/1994 | Kagan et al. |
| 5,313,943 A | 5/1994 | Houser et al. |
| 5,324,255 A | 6/1994 | Passafaro et al. |
| 5,324,284 A | 6/1994 | Imran |
| 5,331,947 A | 7/1994 | Shturman |
| 5,336,178 A * | 8/1994 | Kaplan ............... A61B 8/12 604/103.01 |
| 5,343,936 A | 9/1994 | Beatenbough et al. |
| 5,344,398 A | 9/1994 | Hara |
| 5,345,936 A | 9/1994 | Pomeranz et al. |
| 5,348,554 A | 9/1994 | Imran et al. |
| 5,366,443 A | 11/1994 | Eggers et al. |
| 5,368,591 A | 11/1994 | Lennox et al. |
| 5,370,644 A | 12/1994 | Langberg |
| 5,370,675 A | 12/1994 | Edwards et al. |
| 5,370,679 A | 12/1994 | Atlee, III |
| 5,372,603 A | 12/1994 | Acker et al. |
| 5,374,287 A | 12/1994 | Rubin |
| 5,379,765 A | 1/1995 | Kajiwara et al. |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,405,362 A | 4/1995 | Kramer et al. |
| 5,405,366 A | 4/1995 | Fox et al. |
| 5,409,483 A | 4/1995 | Campbell et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,432,092 A | 7/1995 | Bailey et al. |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,454,840 A | 10/1995 | Krakovsky et al. |
| 5,456,667 A | 10/1995 | Ham et al. |
| 5,458,596 A | 10/1995 | Lax et al. |
| 5,465,717 A | 11/1995 | Imran et al. |
| 5,470,352 A | 11/1995 | Rappaport |
| 5,471,982 A | 12/1995 | Edwards et al. |
| 5,474,530 A | 12/1995 | Passafaro et al. |
| 5,478,309 A | 12/1995 | Sweezer et al. |
| 5,478,578 A | 12/1995 | Arnold et al. |
| 5,496,271 A | 3/1996 | Burton et al. |
| 5,496,304 A | 3/1996 | Chasan |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,540,730 A | 7/1996 | Terry, Jr. et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,553,611 A | 9/1996 | Budd et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,620,463 A | 4/1997 | Drolet |
| 5,623,940 A | 4/1997 | Daikuzono |
| 5,624,392 A | 4/1997 | Saab |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,630,813 A | 5/1997 | Kieturakis |
| 5,634,471 A | 6/1997 | Fairfax et al. |
| 5,641,326 A | 6/1997 | Adams |
| 5,642,730 A * | 7/1997 | Baran ............... A61M 16/0463 128/207.14 |
| 5,647,870 A | 7/1997 | Kordis et al. |
| 5,658,278 A | 8/1997 | Imran et al. |
| 5,658,322 A | 8/1997 | Fleming |
| 5,658,549 A | 8/1997 | Akehurst et al. |

(56) References Cited

U.S. PATENT DOCUMENTS

| | | | |
|---|---|---|---|
| 5,660,175 | A | 8/1997 | Dayal |
| 5,662,108 | A | 9/1997 | Budd et al. |
| 5,669,930 | A | 9/1997 | Igarashi |
| 5,669,932 | A | 9/1997 | Fischell et al. |
| 5,674,472 | A | 10/1997 | Akehurst et al. |
| 5,678,535 | A | 10/1997 | DiMarco |
| 5,680,860 | A | 10/1997 | Imran |
| 5,681,280 | A | 10/1997 | Rusk et al. |
| 5,681,308 | A | 10/1997 | Edwards et al. |
| 5,687,723 | A | 11/1997 | Avitall |
| 5,688,267 | A | 11/1997 | Panescu et al. |
| 5,690,692 | A | 11/1997 | Fleming |
| 5,693,078 | A | 12/1997 | Desai et al. |
| 5,694,934 | A | 12/1997 | Edelman |
| 5,695,471 | A | 12/1997 | Wampler |
| 5,699,799 | A | 12/1997 | Xu et al. |
| 5,702,386 | A | 12/1997 | Stern et al. |
| 5,707,218 | A | 1/1998 | Maher et al. |
| 5,707,336 | A | 1/1998 | Rubin |
| 5,707,352 | A | 1/1998 | Sekins et al. |
| 5,707,400 | A | 1/1998 | Terry, Jr. et al. |
| 5,722,401 | A | 3/1998 | Pietroski et al. |
| 5,722,403 | A | 3/1998 | McGee et al. |
| 5,722,416 | A | 3/1998 | Swanson et al. |
| 5,725,525 | A | 3/1998 | Kordis |
| 5,727,569 | A | 3/1998 | Benetti et al. |
| 5,728,094 | A | 3/1998 | Edwards |
| 5,730,128 | A | 3/1998 | Pomeranz et al. |
| 5,730,704 | A | 3/1998 | Avitall |
| 5,730,726 | A | 3/1998 | Klingenstein |
| 5,730,741 | A | 3/1998 | Horzewski et al. |
| 5,733,319 | A | 3/1998 | Neilson et al. |
| 5,735,846 | A | 4/1998 | Panescu et al. |
| 5,740,808 | A | 4/1998 | Panescu et al. |
| 5,741,248 | A | 4/1998 | Stern et al. |
| 5,746,224 | A | 5/1998 | Edwards |
| 5,752,518 | A | 5/1998 | McGee et al. |
| 5,755,714 | A | 5/1998 | Murphy-Chutorian |
| 5,755,753 | A | 5/1998 | Knowlton |
| 5,759,158 | A | 6/1998 | Swanson |
| 5,765,568 | A | 6/1998 | Sweezer, Jr. et al. |
| 5,766,605 | A * | 6/1998 | Sanders ............ A61K 38/4893 424/236.1 |
| 5,769,846 | A | 6/1998 | Edwards et al. |
| 5,772,590 | A | 6/1998 | Webster, Jr. |
| 5,779,669 | A | 7/1998 | Haissaguerre et al. |
| 5,779,698 | A | 7/1998 | Clayman et al. |
| 5,782,239 | A | 7/1998 | Webster, Jr. |
| 5,782,797 | A | 7/1998 | Schweich, Jr. et al. |
| 5,782,827 | A | 7/1998 | Gough et al. |
| 5,782,848 | A | 7/1998 | Lennox |
| 5,782,899 | A | 7/1998 | Imran |
| 5,792,064 | A | 8/1998 | Panescu et al. |
| 5,795,303 | A | 8/1998 | Swanson et al. |
| 5,800,375 | A | 9/1998 | Sweezer et al. |
| 5,800,486 | A | 9/1998 | Thome et al. |
| 5,807,306 | A | 9/1998 | Shapland et al. |
| 5,810,757 | A | 9/1998 | Sweezer, Jr. et al. |
| 5,810,807 | A | 9/1998 | Ganz et al. |
| 5,814,078 | A | 9/1998 | Zhou et al. |
| 5,817,028 | A | 10/1998 | Anderson |
| 5,817,073 | A | 10/1998 | Krespi |
| 5,820,554 | A | 10/1998 | Davis et al. |
| 5,820,589 | A | 10/1998 | Torgerson et al. |
| 5,823,189 | A | 10/1998 | Kordis |
| 5,827,277 | A | 10/1998 | Edwards |
| 5,833,651 | A | 11/1998 | Donovan et al. |
| 5,833,707 | A | 11/1998 | McIntyre et al. |
| 5,836,874 | A | 11/1998 | Swanson et al. |
| 5,836,905 | A | 11/1998 | Lemelson et al. |
| 5,836,947 | A | 11/1998 | Fleischman et al. |
| 5,837,001 | A | 11/1998 | Mackey |
| 5,843,075 | A | 12/1998 | Taylor |
| 5,843,077 | A | 12/1998 | Edwards |
| 5,843,088 | A | 12/1998 | Barra et al. |
| 5,846,238 | A | 12/1998 | Jackson et al. |
| 5,848,969 | A | 12/1998 | Panescu et al. |
| 5,848,972 | A | 12/1998 | Triedman et al. |
| 5,849,026 | A | 12/1998 | Zhou et al. |
| 5,855,577 | A | 1/1999 | Murphy-Chutorian et al. |
| 5,860,974 | A | 1/1999 | Abele |
| 5,863,291 | A | 1/1999 | Schaer |
| 5,865,791 | A | 2/1999 | Whayne et al. |
| 5,868,740 | A | 2/1999 | Leveen et al. |
| 5,871,443 | A | 2/1999 | Edwards et al. |
| 5,871,483 | A | 2/1999 | Jackson et al. |
| 5,871,523 | A | 2/1999 | Fleischman et al. |
| 5,873,852 | A | 2/1999 | Vigil et al. |
| 5,873,865 | A | 2/1999 | Horzewski et al. |
| 5,876,340 | A | 3/1999 | Tu et al. |
| 5,876,399 | A | 3/1999 | Chia et al. |
| 5,881,727 | A | 3/1999 | Edwards |
| 5,882,346 | A | 3/1999 | Pomeranz et al. |
| 5,891,027 | A | 4/1999 | Tu et al. |
| 5,891,135 | A | 4/1999 | Jackson et al. |
| 5,891,136 | A | 4/1999 | McGee et al. |
| 5,891,138 | A | 4/1999 | Tu et al. |
| 5,891,182 | A | 4/1999 | Fleming |
| 5,893,847 | A | 4/1999 | Kordis |
| 5,893,887 | A | 4/1999 | Jayaraman |
| 5,897,554 | A | 4/1999 | Chia et al. |
| 5,899,882 | A | 5/1999 | Waksman et al. |
| 5,902,268 | A | 5/1999 | Saab |
| 5,904,651 | A | 5/1999 | Swanson et al. |
| 5,904,711 | A | 5/1999 | Flom et al. |
| 5,906,636 | A | 5/1999 | Casscells, III et al. |
| 5,908,445 | A | 6/1999 | Whayne et al. |
| 5,908,446 | A | 6/1999 | Imran |
| 5,908,839 | A | 6/1999 | Levitt et al. |
| 5,911,218 | A | 6/1999 | DiMarco |
| 5,916,235 | A | 6/1999 | Guglielmi |
| 5,919,147 | A | 7/1999 | Jain |
| 5,919,172 | A | 7/1999 | Golba, Jr. |
| 5,924,424 | A | 7/1999 | Stevens et al. |
| 5,928,228 | A | 7/1999 | Kordis et al. |
| 5,931,806 | A | 8/1999 | Shimada |
| 5,931,835 | A | 8/1999 | Mackey |
| 5,935,079 | A | 8/1999 | Swanson et al. |
| 5,941,869 | A | 8/1999 | Patterson et al. |
| 5,951,494 | A | 9/1999 | Wang et al. |
| 5,951,546 | A | 9/1999 | Lorentzen |
| 5,954,661 | A | 9/1999 | Greenspon et al. |
| 5,954,662 | A | 9/1999 | Swanson et al. |
| 5,954,717 | A | 9/1999 | Behl et al. |
| 5,956,501 | A | 9/1999 | Brown |
| 5,957,919 | A | 9/1999 | Laufer |
| 5,957,961 | A | 9/1999 | Maguire et al. |
| 5,964,223 | A | 10/1999 | Baran |
| 5,964,753 | A | 10/1999 | Edwards |
| 5,964,796 | A | 10/1999 | Imran |
| 5,971,983 | A | 10/1999 | Lesh |
| 5,972,026 | A | 10/1999 | Laufer et al. |
| 5,976,175 | A | 11/1999 | Hirano et al. |
| 5,976,709 | A | 11/1999 | Kageyama et al. |
| 5,979,456 | A | 11/1999 | Magovern |
| 5,980,563 | A | 11/1999 | Tu et al. |
| 5,984,917 | A | 11/1999 | Fleischman et al. |
| 5,984,971 | A | 11/1999 | Faccioli et al. |
| 5,989,545 | A | 11/1999 | Foster et al. |
| 5,991,650 | A | 11/1999 | Swanson et al. |
| 5,992,419 | A | 11/1999 | Sterzer et al. |
| 5,993,462 | A | 11/1999 | Pomeranz et al. |
| 5,995,873 | A | 11/1999 | Rhodes |
| 5,997,534 | A | 12/1999 | Tu et al. |
| 5,999,855 | A | 12/1999 | DiMarco |
| 6,001,054 | A | 12/1999 | Regulla et al. |
| 6,003,517 | A | 12/1999 | Sheffield et al. |
| 6,004,269 | A | 12/1999 | Crowley et al. |
| 6,006,134 | A | 12/1999 | Hill et al. |
| 6,006,755 | A | 12/1999 | Edwards |
| 6,008,211 | A | 12/1999 | Robinson et al. |
| 6,009,877 | A | 1/2000 | Edwards |
| 6,010,500 | A | 1/2000 | Sherman et al. |
| 6,014,579 | A | 1/2000 | Pomeranz et al. |

(56) References Cited

U.S. PATENT DOCUMENTS

| | | |
|---|---|---|
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,043,273 A | 3/2000 | Duhaylongsod |
| 6,045,549 A | 4/2000 | Smethers et al. |
| 6,045,550 A | 4/2000 | Simpson et al. |
| 6,050,992 A | 4/2000 | Nichols |
| 6,052,607 A | 4/2000 | Edwards et al. |
| 6,053,172 A | 4/2000 | Hovda et al. |
| 6,053,909 A | 4/2000 | Shadduck |
| 6,056,744 A | 5/2000 | Edwards |
| 6,056,745 A | 5/2000 | Panescu et al. |
| 6,056,769 A | 5/2000 | Epstein et al. |
| 6,060,454 A | 5/2000 | Duhaylongsod |
| 6,063,078 A | 5/2000 | Wittkampf |
| 6,063,768 A | 5/2000 | First |
| 6,071,280 A | 6/2000 | Edwards et al. |
| 6,071,281 A | 6/2000 | Burnside et al. |
| 6,071,282 A | 6/2000 | Fleischman |
| 6,081,749 A | 6/2000 | Ingle et al. |
| 6,083,249 A | 7/2000 | Familoni |
| 6,083,255 A | 7/2000 | Laufer et al. |
| 6,087,394 A | 7/2000 | Duhaylongsod |
| 6,090,104 A | 7/2000 | Webster, Jr. |
| 6,091,995 A | 7/2000 | Ingle et al. |
| 6,092,528 A | 7/2000 | Edwards |
| 6,097,985 A | 8/2000 | Kasevich et al. |
| 6,101,412 A | 8/2000 | Duhaylongsod |
| 6,102,886 A | 8/2000 | Lundquist et al. |
| 6,106,524 A | 8/2000 | Eggers et al. |
| 6,117,101 A | 9/2000 | Diederich et al. |
| 6,123,702 A | 9/2000 | Swanson et al. |
| 6,123,703 A | 9/2000 | Tu et al. |
| 6,123,718 A | 9/2000 | Tu et al. |
| 6,125,301 A | 9/2000 | Capel |
| 6,127,410 A | 10/2000 | Duhaylongsod |
| 6,129,726 A | 10/2000 | Edwards et al. |
| 6,135,997 A | 10/2000 | Laufer et al. |
| 6,139,527 A | 10/2000 | Laufer et al. |
| 6,139,571 A | 10/2000 | Fuller et al. |
| 6,139,845 A | 10/2000 | Donovan |
| 6,141,589 A | 10/2000 | Duhaylongsod |
| 6,142,993 A | 11/2000 | Whayne et al. |
| 6,143,013 A | 11/2000 | Samson et al. |
| 6,143,277 A | 11/2000 | Ashurst et al. |
| 6,149,647 A | 11/2000 | Tu et al. |
| 6,152,143 A | 11/2000 | Edwards |
| 6,152,899 A | 11/2000 | Farley et al. |
| 6,152,953 A | 11/2000 | Hipskind |
| 6,159,194 A | 12/2000 | Eggers et al. |
| 6,163,716 A | 12/2000 | Edwards et al. |
| 6,174,323 B1 | 1/2001 | Biggs et al. |
| 6,179,833 B1 | 1/2001 | Taylor |
| 6,183,468 B1 | 2/2001 | Swanson et al. |
| 6,197,013 B1 | 3/2001 | Reed et al. |
| 6,198,970 B1 | 3/2001 | Freed et al. |
| 6,200,311 B1 | 3/2001 | Danek et al. |
| 6,200,332 B1 | 3/2001 | Del |
| 6,200,333 B1 | 3/2001 | Laufer |
| 6,203,562 B1 | 3/2001 | Ohkubo |
| 6,210,367 B1 | 4/2001 | Carr |
| 6,212,432 B1 | 4/2001 | Matsuura |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,216,704 B1 | 4/2001 | Ingle et al. |
| 6,217,576 B1 | 4/2001 | Tu et al. |
| 6,226,543 B1 | 5/2001 | Gilboa et al. |
| 6,230,052 B1 | 5/2001 | Wolff et al. |
| 6,231,595 B1 | 5/2001 | Dobak, III |
| 6,235,024 B1 | 5/2001 | Tu |
| 6,240,307 B1 | 5/2001 | Beatty et al. |
| 6,241,727 B1 | 6/2001 | Tu et al. |
| 6,245,065 B1 | 6/2001 | Panescu et al. |
| 6,251,368 B1 | 6/2001 | Akehurst et al. |
| 6,253,762 B1 | 7/2001 | Britto |
| 6,254,598 B1 | 7/2001 | Edwards et al. |
| 6,254,599 B1 | 7/2001 | Lesh et al. |
| 6,258,083 B1 | 7/2001 | Daniel et al. |
| 6,258,087 B1 | 7/2001 | Edwards et al. |
| 6,264,653 B1 | 7/2001 | Falwell |
| 6,265,379 B1 | 7/2001 | Donovan |
| 6,269,813 B1 | 8/2001 | Fitzgerald et al. |
| 6,270,476 B1 | 8/2001 | Santoianni et al. |
| 6,273,886 B1 | 8/2001 | Edwards et al. |
| 6,273,907 B1 | 8/2001 | Laufer |
| 6,283,987 B1 | 9/2001 | Laird et al. |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 * | 10/2001 | Laufer ............... A61B 18/1492 607/101 |
| 6,302,780 B1 | 10/2001 | Ahn et al. |
| 6,302,870 B1 | 10/2001 | Jacobsen et al. |
| 6,303,509 B1 | 10/2001 | Chen et al. |
| 6,306,423 B1 | 10/2001 | Donovan et al. |
| 6,315,173 B1 | 11/2001 | Di et al. |
| 6,315,778 B1 | 11/2001 | Gambale et al. |
| 6,317,615 B1 | 11/2001 | KenKnight et al. |
| 6,322,559 B1 | 11/2001 | Daulton et al. |
| 6,322,584 B2 | 11/2001 | Ingle et al. |
| 6,325,798 B1 | 12/2001 | Edwards et al. |
| 6,327,503 B1 | 12/2001 | Familoni |
| 6,338,727 B1 | 1/2002 | Noda et al. |
| 6,338,836 B1 | 1/2002 | Kuth et al. |
| 6,341,236 B1 | 1/2002 | Osorio et al. |
| 6,346,104 B2 | 2/2002 | Daly et al. |
| 6,355,031 B1 | 3/2002 | Edwards et al. |
| 6,356,786 B1 | 3/2002 | Rezai et al. |
| 6,356,787 B1 | 3/2002 | Rezai et al. |
| 6,357,447 B1 | 3/2002 | Swanson et al. |
| 6,358,245 B1 | 3/2002 | Edwards et al. |
| 6,358,926 B2 | 3/2002 | Donovan |
| 6,361,554 B1 | 3/2002 | Brisken |
| 6,363,937 B1 | 4/2002 | Hovda et al. |
| 6,366,814 B1 | 4/2002 | Boveja et al. |
| 6,379,352 B1 | 4/2002 | Reynolds et al. |
| 6,383,509 B1 | 5/2002 | Donovan et al. |
| 6,394,956 B1 | 5/2002 | Chandrasekaran et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,411,852 B1 | 6/2002 | Danek et al. |
| 6,414,018 B1 | 7/2002 | Duhaylongsod |
| 6,416,511 B1 | 7/2002 | Lesh et al. |
| 6,416,740 B1 | 7/2002 | Unger |
| 6,423,058 B1 | 7/2002 | Edwards et al. |
| 6,423,105 B1 | 7/2002 | Iijima et al. |
| 6,424,864 B1 | 7/2002 | Matsuura |
| 6,425,877 B1 | 7/2002 | Edwards |
| 6,425,887 B1 | 7/2002 | McGuckin et al. |
| 6,425,895 B1 | 7/2002 | Swanson et al. |
| 6,432,092 B2 | 8/2002 | Miller |
| 6,436,130 B1 | 8/2002 | Philips et al. |
| 6,438,423 B1 | 8/2002 | Rezai et al. |
| 6,440,128 B1 | 8/2002 | Edwards et al. |
| 6,440,129 B1 | 8/2002 | Simpson |
| 6,442,435 B2 | 8/2002 | King et al. |
| 6,447,505 B2 | 9/2002 | McGovern et al. |
| 6,447,785 B1 | 9/2002 | Donovan |
| 6,448,231 B2 | 9/2002 | Graham |
| 6,456,932 B2 | 9/2002 | Yagyu |
| 6,458,121 B1 | 10/2002 | Rosenstock et al. |
| 6,460,545 B2 | 10/2002 | Kordis |
| 6,464,680 B1 | 10/2002 | Brisken et al. |
| 6,464,697 B1 | 10/2002 | Edwards et al. |
| 6,475,160 B1 | 11/2002 | Sher |

(56) References Cited

U.S. PATENT DOCUMENTS

| | | |
|---|---|---|
| 6,480,746 B1 | 11/2002 | Ingle et al. |
| 6,485,416 B1 | 11/2002 | Platt et al. |
| 6,488,673 B1 * | 12/2002 | Laufer .................. A61B 18/00 604/516 |
| 6,488,679 B1 | 12/2002 | Swanson et al. |
| 6,491,710 B2 | 12/2002 | Satake |
| 6,493,589 B1 | 12/2002 | Medhkour et al. |
| 6,494,880 B1 | 12/2002 | Swanson et al. |
| 6,496,737 B2 | 12/2002 | Rudie et al. |
| 6,496,738 B2 | 12/2002 | Carr |
| 6,506,399 B2 | 1/2003 | Donovan |
| 6,510,969 B2 | 1/2003 | Di et al. |
| 6,514,246 B1 | 2/2003 | Swanson et al. |
| 6,514,290 B1 | 2/2003 | Loomas |
| 6,519,488 B2 | 2/2003 | KenKnight et al. |
| 6,522,913 B2 | 2/2003 | Swanson et al. |
| 6,524,555 B1 | 2/2003 | Ashurst et al. |
| 6,526,320 B2 | 2/2003 | Mitchell |
| 6,526,976 B1 * | 3/2003 | Baran ............... A61M 16/0463 128/200.14 |
| 6,529,756 B1 | 3/2003 | Phan et al. |
| 6,532,388 B1 | 3/2003 | Hill et al. |
| 6,533,780 B1 | 3/2003 | Laird et al. |
| 6,536,427 B2 | 3/2003 | Davies et al. |
| 6,544,226 B1 | 4/2003 | Gaiser et al. |
| 6,544,262 B2 | 4/2003 | Fleischman |
| 6,546,928 B1 | 4/2003 | Ashurst et al. |
| 6,546,932 B1 | 4/2003 | Nahon et al. |
| 6,546,934 B1 | 4/2003 | Ingle et al. |
| 6,547,776 B1 | 4/2003 | Gaiser et al. |
| 6,547,788 B1 | 4/2003 | Maguire et al. |
| 6,549,808 B1 | 4/2003 | Gisel et al. |
| 6,551,274 B2 | 4/2003 | Heiner |
| 6,551,310 B1 | 4/2003 | Ganz et al. |
| 6,558,333 B2 | 5/2003 | Gilboa et al. |
| 6,558,378 B2 | 5/2003 | Sherman et al. |
| 6,558,381 B2 | 5/2003 | Ingle et al. |
| 6,562,034 B2 | 5/2003 | Edwards et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,587,718 B2 | 7/2003 | Talpade |
| 6,587,719 B1 | 7/2003 | Barrett et al. |
| 6,587,731 B1 | 7/2003 | Ingle et al. |
| 6,589,235 B2 | 7/2003 | Wong et al. |
| 6,589,238 B2 | 7/2003 | Edwards et al. |
| 6,593,130 B1 | 7/2003 | Sen et al. |
| 6,599,311 B1 | 7/2003 | Biggs et al. |
| 6,601,581 B1 | 8/2003 | Babaev |
| 6,603,996 B1 | 8/2003 | Beatty et al. |
| 6,610,054 B1 | 8/2003 | Edwards et al. |
| 6,610,083 B2 | 8/2003 | Keller et al. |
| 6,610,713 B2 | 8/2003 | Tracey |
| 6,613,002 B1 | 9/2003 | Clark et al. |
| 6,613,045 B1 | 9/2003 | Laufer et al. |
| 6,620,159 B2 | 9/2003 | Hegde |
| 6,620,415 B2 | 9/2003 | Donovan |
| 6,622,047 B2 | 9/2003 | Barrett et al. |
| 6,623,742 B2 | 9/2003 | Voet |
| 6,626,855 B1 | 9/2003 | Weng et al. |
| 6,626,903 B2 | 9/2003 | McGuckin et al. |
| 6,629,535 B2 | 10/2003 | Ingle et al. |
| 6,629,951 B2 | 10/2003 | Laufer et al. |
| 6,632,440 B1 | 10/2003 | Quinn et al. |
| 6,633,779 B1 | 10/2003 | Schuler et al. |
| 6,634,363 B1 | 10/2003 | Danek et al. |
| 6,635,054 B2 | 10/2003 | Fjield et al. |
| 6,635,056 B2 | 10/2003 | Kadhiresan et al. |
| 6,638,273 B1 | 10/2003 | Farley et al. |
| 6,640,119 B1 | 10/2003 | Budd et al. |
| 6,640,120 B1 | 10/2003 | Swanson et al. |
| 6,645,200 B1 | 11/2003 | Koblish et al. |
| 6,645,496 B2 | 11/2003 | Aoki et al. |
| 6,647,617 B1 | 11/2003 | Beatty et al. |
| 6,648,881 B2 | 11/2003 | KenKnight et al. |
| 6,649,161 B1 | 11/2003 | Donovan |
| 6,652,517 B1 | 11/2003 | Hall et al. |
| 6,652,548 B2 | 11/2003 | Evans et al. |
| 6,656,960 B2 | 12/2003 | Puskas |
| 6,658,279 B2 | 12/2003 | Swanson et al. |
| 6,663,622 B1 | 12/2003 | Foley et al. |
| 6,666,858 B2 | 12/2003 | Lafontaine |
| 6,669,693 B2 | 12/2003 | Friedman |
| 6,673,068 B1 | 1/2004 | Berube |
| 6,673,070 B2 | 1/2004 | Edwards et al. |
| 6,675,047 B1 | 1/2004 | Konoplev et al. |
| 6,676,686 B2 | 1/2004 | Naganuma |
| 6,681,136 B2 | 1/2004 | Schuler et al. |
| 6,692,492 B2 | 2/2004 | Simpson et al. |
| 6,692,494 B1 | 2/2004 | Cooper et al. |
| 6,699,180 B2 | 3/2004 | Kobayashi |
| 6,699,243 B2 | 3/2004 | West et al. |
| 6,708,064 B2 | 3/2004 | Rezai |
| 6,711,436 B1 | 3/2004 | Duhaylongsod |
| 6,712,074 B2 | 3/2004 | Edwards et al. |
| 6,712,812 B2 | 3/2004 | Roschak et al. |
| 6,712,814 B2 | 3/2004 | Edwards et al. |
| 6,714,822 B2 | 3/2004 | King et al. |
| 6,719,685 B2 | 4/2004 | Fujikura et al. |
| 6,719,694 B2 | 4/2004 | Weng et al. |
| 6,723,053 B2 | 4/2004 | Ackerman et al. |
| 6,723,091 B2 | 4/2004 | Goble et al. |
| 6,726,677 B1 | 4/2004 | Flaherty et al. |
| 6,728,562 B1 | 4/2004 | Budd et al. |
| 6,735,471 B2 | 5/2004 | Hill et al. |
| 6,735,475 B1 | 5/2004 | Whitehurst et al. |
| 6,740,321 B1 | 5/2004 | Donovan |
| 6,743,197 B1 | 6/2004 | Edwards |
| 6,743,413 B1 | 6/2004 | Schultz et al. |
| 6,749,604 B1 | 6/2004 | Eggers et al. |
| 6,749,606 B2 | 6/2004 | Keast et al. |
| 6,752,765 B1 | 6/2004 | Jensen et al. |
| 6,755,026 B2 | 6/2004 | Wallach |
| 6,755,849 B1 | 6/2004 | Gowda et al. |
| 6,767,347 B2 | 7/2004 | Sharkey et al. |
| 6,767,544 B2 | 7/2004 | Brooks et al. |
| 6,770,070 B1 | 8/2004 | Balbierz |
| 6,772,013 B1 | 8/2004 | Ingle et al. |
| 6,773,711 B2 | 8/2004 | Voet et al. |
| 6,776,991 B2 | 8/2004 | Naumann |
| 6,777,423 B2 | 8/2004 | Banholzer et al. |
| 6,778,854 B2 | 8/2004 | Puskas |
| 6,780,183 B2 | 8/2004 | Jimenez et al. |
| 6,786,889 B1 | 9/2004 | Musbach et al. |
| 6,802,843 B2 | 10/2004 | Truckai et al. |
| 6,805,131 B2 | 10/2004 | Kordis |
| 6,819,956 B2 | 11/2004 | DiLorenzo |
| 6,826,420 B1 | 11/2004 | Beatty et al. |
| 6,826,421 B1 | 11/2004 | Beatty et al. |
| 6,827,931 B1 | 12/2004 | Donovan |
| 6,836,688 B2 | 12/2004 | Ingle et al. |
| 6,837,888 B2 | 1/2005 | Ciarrocca et al. |
| 6,838,429 B2 | 1/2005 | Paslin |
| 6,838,434 B2 | 1/2005 | Voet |
| 6,838,471 B2 | 1/2005 | Tracey |
| 6,840,243 B2 | 1/2005 | Deem et al. |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,861,058 B2 | 3/2005 | Aoki et al. |
| 6,866,662 B2 | 3/2005 | Fuimaono et al. |
| 6,871,092 B2 | 3/2005 | Piccone |
| 6,872,206 B2 | 3/2005 | Edwards et al. |
| 6,872,397 B2 | 3/2005 | Aoki et al. |
| 6,878,156 B1 | 4/2005 | Noda |
| 6,881,213 B2 | 4/2005 | Ryan et al. |
| 6,885,888 B2 | 4/2005 | Rezai |
| 6,890,347 B2 | 5/2005 | Machold et al. |

(56) References Cited

U.S. PATENT DOCUMENTS

| | | |
|---|---|---|
| 6,893,436 B2 | 5/2005 | Woodard et al. |
| 6,893,438 B2 | 5/2005 | Hall et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,908,462 B2 | 6/2005 | Joye et al. |
| 6,908,928 B2 | 6/2005 | Banholzer et al. |
| 6,913,616 B2 | 7/2005 | Hamilton et al. |
| 6,917,834 B2 | 7/2005 | Koblish et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,939,309 B1 | 9/2005 | Beatty et al. |
| 6,939,345 B2 | 9/2005 | KenKnight et al. |
| 6,939,346 B2 | 9/2005 | Kannenberg et al. |
| 6,947,785 B1 | 9/2005 | Beatty et al. |
| 6,954,977 B2 | 10/2005 | Maguire et al. |
| 6,955,661 B1 * | 10/2005 | Herweck ............... A61L 29/041 604/103.01 |
| 6,957,106 B2 | 10/2005 | Schuler et al. |
| 6,961,622 B2 | 11/2005 | Gilbert |
| 6,970,742 B2 | 11/2005 | Mann et al. |
| RE38,912 E | 12/2005 | Walz et al. |
| 6,971,395 B2 | 12/2005 | Edwards et al. |
| 6,974,224 B2 | 12/2005 | Thomas-Benedict |
| 6,974,456 B2 | 12/2005 | Edwards et al. |
| 6,974,578 B1 | 12/2005 | Aoki et al. |
| 6,978,168 B2 | 12/2005 | Beatty et al. |
| 6,978,174 B2 | 12/2005 | Gelfand et al. |
| 6,990,370 B1 | 1/2006 | Beatty et al. |
| 6,994,706 B2 | 2/2006 | Chornenky et al. |
| 6,997,189 B2 | 2/2006 | Biggs et al. |
| 7,004,942 B2 | 2/2006 | Laird et al. |
| 7,022,088 B2 | 4/2006 | Keast et al. |
| 7,022,105 B1 | 4/2006 | Edwards |
| 7,027,869 B2 | 4/2006 | Danek et al. |
| 7,043,307 B1 | 5/2006 | Zelickson et al. |
| 7,070,800 B2 | 7/2006 | Bechtold-Peters et al. |
| 7,072,720 B2 | 7/2006 | Puskas |
| 7,083,614 B2 | 8/2006 | Fjield et al. |
| 7,093,595 B2 | 8/2006 | Nesbitt et al. |
| 7,101,368 B2 | 9/2006 | Lafontaine |
| 7,101,387 B2 | 9/2006 | Garabedian et al. |
| 7,104,987 B2 | 9/2006 | Biggs et al. |
| 7,104,990 B2 | 9/2006 | Jenkins et al. |
| 7,112,198 B2 | 9/2006 | Satake |
| 7,118,568 B2 | 10/2006 | Hassett et al. |
| 7,122,031 B2 | 10/2006 | Edwards et al. |
| 7,122,033 B2 | 10/2006 | Wood |
| 7,125,407 B2 | 10/2006 | Edwards et al. |
| 7,131,445 B2 | 11/2006 | Amoah |
| 7,142,910 B2 | 11/2006 | Puskas |
| 7,150,745 B2 | 12/2006 | Stern et al. |
| 7,162,303 B2 | 1/2007 | Levin et al. |
| 7,165,551 B2 | 1/2007 | Edwards et al. |
| 7,167,757 B2 | 1/2007 | Ingle et al. |
| 7,175,644 B2 | 2/2007 | Cooper et al. |
| 7,179,257 B2 | 2/2007 | West et al. |
| 7,184,811 B2 | 2/2007 | Phan et al. |
| 7,186,251 B2 | 3/2007 | Malecki et al. |
| 7,187,964 B2 | 3/2007 | Khoury |
| 7,187,973 B2 | 3/2007 | Hauck |
| 7,189,208 B1 | 3/2007 | Beatty et al. |
| 7,198,635 B2 | 4/2007 | Danaek et al. |
| 7,200,445 B1 | 4/2007 | Dalbec et al. |
| 7,229,469 B1 | 6/2007 | Witzel et al. |
| 7,238,357 B2 | 7/2007 | Barron |
| 7,241,295 B2 | 7/2007 | Maguire |
| 7,255,693 B1 | 8/2007 | Johnston et al. |
| RE39,820 E | 9/2007 | Banholzer et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,289,843 B2 | 10/2007 | Beatty et al. |
| 7,291,146 B2 | 11/2007 | Steinke et al. |
| 7,292,890 B2 | 11/2007 | Whitehurst et al. |
| 7,309,707 B2 | 12/2007 | Bender et al. |
| 7,310,552 B2 | 12/2007 | Puskas |
| RE40,045 E | 2/2008 | Palmer |
| 7,326,207 B2 | 2/2008 | Edwards |
| 7,344,535 B2 | 3/2008 | Stern et al. |
| 7,371,231 B2 | 5/2008 | Rioux et al. |
| 7,393,330 B2 | 7/2008 | Keast et al. |
| 7,393,350 B2 | 7/2008 | Maurice |
| 7,394,976 B2 | 7/2008 | Entenman et al. |
| 7,402,172 B2 | 7/2008 | Chin et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,430,449 B2 | 9/2008 | Aldrich et al. |
| 7,462,162 B2 | 12/2008 | Phan et al. |
| 7,462,179 B2 | 12/2008 | Edwards et al. |
| 7,473,273 B2 | 1/2009 | Campbell |
| 7,477,945 B2 | 1/2009 | Rezai et al. |
| 7,483,755 B2 | 1/2009 | Ingle et al. |
| 7,493,160 B2 | 2/2009 | Weber et al. |
| 7,494,661 B2 | 2/2009 | Sanders |
| 7,507,234 B2 | 3/2009 | Utley et al. |
| 7,507,238 B2 | 3/2009 | Utley et al. |
| 7,517,320 B2 | 4/2009 | Wibowo et al. |
| 7,530,979 B2 | 5/2009 | Ganz et al. |
| 7,532,938 B2 | 5/2009 | Machado et al. |
| 7,542,802 B2 | 6/2009 | Danek et al. |
| 7,553,307 B2 | 6/2009 | Bleich et al. |
| 7,556,624 B2 | 7/2009 | Laufer et al. |
| 7,559,890 B2 | 7/2009 | Wallace et al. |
| 7,572,245 B2 | 8/2009 | Herweck et al. |
| 7,585,296 B2 | 9/2009 | Edward et al. |
| 7,588,549 B2 | 9/2009 | Eccleston |
| 7,594,925 B2 | 9/2009 | Danek et al. |
| 7,608,275 B2 | 10/2009 | Deem et al. |
| 7,613,515 B2 | 11/2009 | Knudson et al. |
| 7,617,005 B2 | 11/2009 | Demarais et al. |
| 7,620,451 B2 | 11/2009 | Demarais et al. |
| 7,628,789 B2 | 12/2009 | Soltesz et al. |
| 7,632,268 B2 | 12/2009 | Utley et al. |
| 7,641,632 B2 | 1/2010 | Noda et al. |
| 7,641,633 B2 | 1/2010 | Laufer et al. |
| 7,648,500 B2 | 1/2010 | Edwards et al. |
| 7,653,438 B2 | 1/2010 | Deem et al. |
| 7,684,865 B2 | 3/2010 | Aldrich et al. |
| 7,689,290 B2 | 3/2010 | Ingle et al. |
| 7,691,079 B2 | 4/2010 | Gobel et al. |
| RE41,334 E | 5/2010 | Beatty et al. |
| 7,708,712 B2 | 5/2010 | Phan et al. |
| 7,708,768 B2 | 5/2010 | Danek et al. |
| 7,711,430 B2 | 5/2010 | Errico et al. |
| 7,717,948 B2 | 5/2010 | Demarais et al. |
| 7,722,538 B2 | 5/2010 | Khoury |
| 7,725,188 B2 | 5/2010 | Errico et al. |
| 7,734,355 B2 | 6/2010 | Cohen et al. |
| 7,734,535 B1 | 6/2010 | Burns |
| 7,740,017 B2 | 6/2010 | Danek et al. |
| 7,740,631 B2 | 6/2010 | Bleich et al. |
| 7,742,795 B2 | 6/2010 | Stone et al. |
| 7,747,324 B2 | 6/2010 | Errico et al. |
| 7,756,583 B2 | 7/2010 | Demarais et al. |
| 7,765,010 B2 | 7/2010 | Chornenky et al. |
| 7,770,584 B2 | 8/2010 | Danek et al. |
| 7,783,358 B2 | 8/2010 | Aldrich et al. |
| 7,815,590 B2 | 10/2010 | Cooper |
| 7,826,881 B1 | 11/2010 | Beatty et al. |
| 7,831,288 B1 | 11/2010 | Beatty et al. |
| 7,837,676 B2 | 11/2010 | Sinelnikov et al. |
| 7,837,679 B2 | 11/2010 | Biggs et al. |
| 7,841,986 B2 | 11/2010 | He et al. |
| 7,844,338 B2 | 11/2010 | Knudson et al. |
| 7,853,331 B2 | 12/2010 | Kaplan et al. |
| 7,854,734 B2 | 12/2010 | Biggs et al. |
| 7,854,740 B2 | 12/2010 | Carney et al. |
| 7,869,879 B2 | 1/2011 | Errico et al. |
| 7,869,880 B2 | 1/2011 | Errico et al. |
| 7,873,417 B2 | 1/2011 | Demarais et al. |
| 7,877,146 B2 | 1/2011 | Rezai et al. |

(56) References Cited

U.S. PATENT DOCUMENTS

| | | |
|---|---|---|
| 7,904,159 B2 | 3/2011 | Errico et al. |
| 7,906,124 B2 | 3/2011 | Laufer et al. |
| 7,914,448 B2 | 3/2011 | Bob et al. |
| 7,921,855 B2 | 4/2011 | Danek et al. |
| 7,930,012 B2 | 4/2011 | Beatty et al. |
| 7,931,647 B2 | 4/2011 | Wizeman et al. |
| 7,937,143 B2 | 5/2011 | Demarais et al. |
| 7,938,123 B2 | 5/2011 | Danek et al. |
| 7,949,407 B2 | 5/2011 | Kaplan et al. |
| 7,967,782 B2 | 6/2011 | Laufer et al. |
| 7,985,187 B2 | 7/2011 | Wibowo et al. |
| 7,992,572 B2 | 8/2011 | Danek et al. |
| 7,993,336 B2 | 8/2011 | Jackson et al. |
| 8,002,740 B2 | 8/2011 | Willink et al. |
| 8,007,495 B2 | 8/2011 | McDaniel et al. |
| 8,008,127 B2 | 8/2011 | Naito |
| 8,010,197 B2 | 8/2011 | Errico et al. |
| 8,012,149 B2 | 9/2011 | Jackson et al. |
| 8,041,428 B2 | 10/2011 | Errico et al. |
| 8,046,085 B2 | 10/2011 | Knudson et al. |
| 8,052,668 B2 | 11/2011 | Sih |
| 8,088,127 B2 | 1/2012 | Mayse et al. |
| 8,099,167 B1 | 1/2012 | Errico et al. |
| 8,105,817 B2 | 1/2012 | Deem et al. |
| 8,128,595 B2 | 3/2012 | Walker et al. |
| 8,128,617 B2 | 3/2012 | Bencini et al. |
| 8,131,371 B2 | 3/2012 | Demarais et al. |
| 8,133,497 B2 | 3/2012 | Deem et al. |
| 8,152,803 B2 | 4/2012 | Edwards et al. |
| 8,172,827 B2 | 5/2012 | Deem et al. |
| 8,204,598 B2 | 6/2012 | Errico et al. |
| 8,208,998 B2 | 6/2012 | Beatty et al. |
| 8,209,034 B2 | 6/2012 | Simon et al. |
| 8,216,216 B2 | 7/2012 | Warnking et al. |
| 8,226,638 B2 | 7/2012 | Mayse et al. |
| 8,229,564 B2 | 7/2012 | Rezai |
| 8,231,621 B2 | 7/2012 | Hutchins et al. |
| 8,233,988 B2 | 7/2012 | Errico et al. |
| 8,251,992 B2 | 8/2012 | Utley et al. |
| 8,267,094 B2 | 9/2012 | Danek et al. |
| 8,295,902 B2 | 10/2012 | Salahieh et al. |
| 8,303,581 B2 | 11/2012 | Arts et al. |
| 8,313,484 B2 | 11/2012 | Edwards et al. |
| 8,328,798 B2 | 12/2012 | Witzel et al. |
| 8,338,164 B2 | 12/2012 | Deem et al. |
| 8,347,891 B2 | 1/2013 | Demarais et al. |
| 8,357,118 B2 | 1/2013 | Orr |
| 8,364,237 B2 | 1/2013 | Stone et al. |
| 8,371,303 B2 | 2/2013 | Schaner et al. |
| 8,377,055 B2 | 2/2013 | Jackson et al. |
| 8,483,831 B1 | 7/2013 | Hlavka et al. |
| 8,489,192 B1 | 7/2013 | Hlavka et al. |
| 8,660,647 B2 | 2/2014 | Parnis et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,236 B2 | 8/2014 | Orr |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 * | 5/2016 | Deem ............... A61M 11/00 |
| 9,398,933 B2 | 7/2016 | Mayse |
| 9,498,283 B2 | 11/2016 | Deem et al. |
| 9,539,048 B2 | 1/2017 | Hlavka et al. |
| 9,649,153 B2 | 5/2017 | Mayse et al. |
| 9,649,154 B2 | 5/2017 | Mayse et al. |
| 9,662,171 B2 | 5/2017 | Dimmer et al. |
| 9,668,809 B2 | 6/2017 | Mayse et al. |
| 9,675,412 B2 | 6/2017 | Mayse et al. |
| 9,867,986 B2 | 1/2018 | Hlavka et al. |
| 9,931,162 B2 | 4/2018 | Mayse et al. |
| 10,022,529 B2 | 7/2018 | Deem et al. |
| 10,149,714 B2 | 12/2018 | Mayse et al. |
| 10,201,386 B2 | 2/2019 | Mayse et al. |
| 10,206,735 B2 | 2/2019 | Kaveckis et al. |
| 10,252,057 B2 | 4/2019 | Hlavka et al. |
| 2001/0020151 A1 | 9/2001 | Reed et al. |
| 2001/0044596 A1 | 11/2001 | Jaafar |
| 2002/0002387 A1 | 1/2002 | Naganuma |
| 2002/0010495 A1 | 1/2002 | Freed et al. |
| 2002/0013581 A1 | 1/2002 | Edwards et al. |
| 2002/0016344 A1 | 2/2002 | Tracey |
| 2002/0042564 A1 | 4/2002 | Cooper et al. |
| 2002/0042565 A1 | 4/2002 | Cooper et al. |
| 2002/0049370 A1 | 4/2002 | Laufer et al. |
| 2002/0072738 A1 | 6/2002 | Edwards et al. |
| 2002/0082197 A1 | 6/2002 | Aoki et al. |
| 2002/0087153 A1 | 7/2002 | Roschak et al. |
| 2002/0087208 A1 | 7/2002 | Koblish et al. |
| 2002/0091379 A1 | 7/2002 | Danek et al. |
| 2002/0107512 A1 | 8/2002 | Edwards |
| 2002/0107515 A1 | 8/2002 | Edwards et al. |
| 2002/0111386 A1 | 8/2002 | Sekins et al. |
| 2002/0111619 A1 | 8/2002 | Keast et al. |
| 2002/0111620 A1 | 8/2002 | Cooper et al. |
| 2002/0115991 A1* | 8/2002 | Edwards ............... A61B 18/00 606/41 |
| 2002/0116030 A1 | 8/2002 | Rezai |
| 2002/0143302 A1 | 10/2002 | Hinchliffe et al. |
| 2002/0143326 A1 | 10/2002 | Foley et al. |
| 2002/0143373 A1 | 10/2002 | Courtnage et al. |
| 2002/0151888 A1 | 10/2002 | Edwards et al. |
| 2002/0183682 A1 | 12/2002 | Darvish |
| 2002/0198512 A1 | 12/2002 | Seward |
| 2002/0198570 A1 | 12/2002 | Puskas |
| 2002/0198574 A1 | 12/2002 | Gumpert |
| 2003/0018344 A1 | 1/2003 | Kaji et al. |
| 2003/0023287 A1 | 1/2003 | Edwards et al. |
| 2003/0027752 A1 | 2/2003 | Steward et al. |
| 2003/0036755 A1 | 2/2003 | Ginn |
| 2003/0050591 A1 | 3/2003 | Patrick |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0070676 A1 | 4/2003 | Cooper et al. |
| 2003/0074039 A1 | 4/2003 | Puskas |
| 2003/0093069 A1 | 5/2003 | Panescu et al. |
| 2003/0093128 A1 | 5/2003 | Freed et al. |
| 2003/0118327 A1 | 6/2003 | Um et al. |
| 2003/0125786 A1 | 7/2003 | Gliner et al. |
| 2003/0130657 A1 | 7/2003 | Tom et al. |
| 2003/0144572 A1 | 7/2003 | Oschman et al. |
| 2003/0153905 A1 | 8/2003 | Edwards et al. |
| 2003/0159700 A1 | 8/2003 | Laufer et al. |
| 2003/0181949 A1 | 9/2003 | Whale |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. |
| 2003/0208103 A1 | 11/2003 | Sonnenschein et al. |
| 2003/0211121 A1 | 11/2003 | Donovan |
| 2003/0216791 A1 | 11/2003 | Schuler et al. |
| 2003/0216792 A1 | 11/2003 | Levin et al. |
| 2003/0216891 A1 | 11/2003 | Wegener |
| 2003/0225443 A1 | 12/2003 | Kiran et al. |
| 2003/0233099 A1 | 12/2003 | Danaek et al. |
| 2003/0236455 A1 | 12/2003 | Swanson et al. |
| 2004/0006268 A1 | 1/2004 | Gilboa et al. |
| 2004/0009180 A1 | 1/2004 | Donovan |
| 2004/0010289 A1 | 1/2004 | Biggs et al. |
| 2004/0010290 A1 | 1/2004 | Schroeppel et al. |
| 2004/0028676 A1 | 2/2004 | Klein et al. |
| 2004/0029849 A1 | 2/2004 | Schatzberg et al. |
| 2004/0030368 A1 | 2/2004 | Kemeny et al. |
| 2004/0031494 A1 | 2/2004 | Danek et al. |
| 2004/0044390 A1 | 3/2004 | Szeles |

(56) References Cited

U.S. PATENT DOCUMENTS

| | | |
|---|---|---|
| 2004/0059383 A1 | 3/2004 | Puskas |
| 2004/0073201 A1 | 4/2004 | Cooper et al. |
| 2004/0073206 A1 | 4/2004 | Foley et al. |
| 2004/0073278 A1 | 4/2004 | Pachys |
| 2004/0084049 A1 | 5/2004 | Baran |
| 2004/0086531 A1 | 5/2004 | Barron |
| 2004/0087936 A1 | 5/2004 | Stern et al. |
| 2004/0088030 A1 | 5/2004 | Jung et al. |
| 2004/0088036 A1 | 5/2004 | Gilbert |
| 2004/0091880 A1 | 5/2004 | Wiebusch et al. |
| 2004/0106954 A1 | 6/2004 | Whitehurst et al. |
| 2004/0116981 A1 | 6/2004 | Mazar |
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127958 A1 | 7/2004 | Mazar et al. |
| 2004/0142005 A1 | 7/2004 | Brooks et al. |
| 2004/0147921 A1 | 7/2004 | Edwards et al. |
| 2004/0147969 A1 | 7/2004 | Mann et al. |
| 2004/0147988 A1 | 7/2004 | Stephens |
| 2004/0151741 A1 | 8/2004 | Borodic |
| 2004/0153056 A1 | 8/2004 | Muller et al. |
| 2004/0162584 A1 | 8/2004 | Hill et al. |
| 2004/0162597 A1 | 8/2004 | Hamilton et al. |
| 2004/0167509 A1 | 8/2004 | Taimisto |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0175399 A1 | 9/2004 | Schiffman |
| 2004/0176803 A1 | 9/2004 | Whelan et al. |
| 2004/0176805 A1 | 9/2004 | Whelan et al. |
| 2004/0182399 A1 | 9/2004 | Danek et al. |
| 2004/0186435 A1 | 9/2004 | Seward |
| 2004/0204747 A1 | 10/2004 | Kemeny et al. |
| 2004/0213813 A1 | 10/2004 | Ackerman |
| 2004/0213814 A1 | 10/2004 | Ackerman |
| 2004/0215235 A1 | 10/2004 | Jackson et al. |
| 2004/0215289 A1 | 10/2004 | Fukui |
| 2004/0215296 A1 | 10/2004 | Robert et al. |
| 2004/0220556 A1 | 11/2004 | Cooper et al. |
| 2004/0220562 A1 | 11/2004 | Garabedian et al. |
| 2004/0220621 A1 | 11/2004 | Zhou et al. |
| 2004/0226556 A1 | 11/2004 | Deem et al. |
| 2004/0230251 A1 | 11/2004 | Schuler et al. |
| 2004/0230252 A1 | 11/2004 | Kullok et al. |
| 2004/0243118 A1 | 12/2004 | Ayers et al. |
| 2004/0243182 A1 | 12/2004 | Cohen et al. |
| 2004/0248188 A1 | 12/2004 | Sanders |
| 2004/0249401 A1 | 12/2004 | Rabiner et al. |
| 2004/0249416 A1 | 12/2004 | Yun et al. |
| 2004/0253274 A1 | 12/2004 | Voet |
| 2004/0267195 A1 | 12/2004 | Currlin |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0019346 A1 | 1/2005 | Boulis |
| 2005/0021092 A1 | 1/2005 | Yun et al. |
| 2005/0049615 A1 | 3/2005 | Cooper et al. |
| 2005/0056292 A1 | 3/2005 | Cooper |
| 2005/0059153 A1 | 3/2005 | George et al. |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0065553 A1 | 3/2005 | Ben et al. |
| 2005/0065562 A1 | 3/2005 | Rezai et al. |
| 2005/0065567 A1 | 3/2005 | Lee et al. |
| 2005/0065573 A1 | 3/2005 | Rezai |
| 2005/0065574 A1 | 3/2005 | Rezai |
| 2005/0065575 A1 | 3/2005 | Dobak |
| 2005/0065584 A1 | 3/2005 | Schiff et al. |
| 2005/0074461 A1 | 4/2005 | Donovan |
| 2005/0076909 A1 | 4/2005 | Stahmann et al. |
| 2005/0080461 A1 | 4/2005 | Stahmann et al. |
| 2005/0085801 A1 | 4/2005 | Cooper et al. |
| 2005/0090722 A1 | 4/2005 | Perez |
| 2005/0096529 A1 | 5/2005 | Cooper et al. |
| 2005/0096644 A1 | 5/2005 | Hall et al. |
| 2005/0107783 A1 | 5/2005 | Tom et al. |
| 2005/0107829 A1 | 5/2005 | Edwards et al. |
| 2005/0107853 A1 | 5/2005 | Krespi et al. |
| 2005/0125044 A1 | 6/2005 | Tracey et al. |
| 2005/0137518 A1 | 6/2005 | Biggs et al. |
| 2005/0137611 A1 | 6/2005 | Escudero et al. |
| 2005/0137715 A1 | 6/2005 | Phan et al. |
| 2005/0143788 A1 | 6/2005 | Yun et al. |
| 2005/0149146 A1 | 7/2005 | Boveja et al. |
| 2005/0152924 A1 | 7/2005 | Voet |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171396 A1 | 8/2005 | Pankratov et al. |
| 2005/0177144 A1 | 8/2005 | Phan et al. |
| 2005/0177192 A1 | 8/2005 | Rezai et al. |
| 2005/0182288 A1 | 8/2005 | Zabara |
| 2005/0182393 A1 | 8/2005 | Abboud et al. |
| 2005/0183732 A1 | 8/2005 | Edwards |
| 2005/0187579 A1 | 8/2005 | Danek et al. |
| 2005/0193279 A1 | 9/2005 | Daners |
| 2005/0203503 A1 | 9/2005 | Edwards et al. |
| 2005/0222628 A1 | 10/2005 | Krakousky |
| 2005/0222635 A1 | 10/2005 | Krakovsky |
| 2005/0222651 A1 | 10/2005 | Jung, Jr. |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240176 A1 | 10/2005 | Oral et al. |
| 2005/0240241 A1 | 10/2005 | Yun et al. |
| 2005/0245926 A1 | 11/2005 | Edwards et al. |
| 2005/0245992 A1 | 11/2005 | Persen et al. |
| 2005/0251128 A1 | 11/2005 | Amoah |
| 2005/0251213 A1 | 11/2005 | Freeman |
| 2005/0255317 A1 | 11/2005 | Bavaro et al. |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0015151 A1 | 1/2006 | Aldrich |
| 2006/0058692 A1 | 3/2006 | Beatty et al. |
| 2006/0058693 A1 | 3/2006 | Beatty et al. |
| 2006/0058780 A1 | 3/2006 | Edwards et al. |
| 2006/0062808 A1 | 3/2006 | Laufer et al. |
| 2006/0079887 A1 | 4/2006 | Buysse et al. |
| 2006/0084884 A1 | 4/2006 | Beatty et al. |
| 2006/0084966 A1 | 4/2006 | Maguire et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0089637 A1 | 4/2006 | Werneth et al. |
| 2006/0095032 A1 | 5/2006 | Jackson et al. |
| 2006/0100666 A1 | 5/2006 | Wilkinson et al. |
| 2006/0106361 A1 | 5/2006 | Muni et al. |
| 2006/0111755 A1 | 5/2006 | Stone et al. |
| 2006/0116749 A1 | 6/2006 | Willink et al. |
| 2006/0135953 A1 | 6/2006 | Kania et al. |
| 2006/0135984 A1 | 6/2006 | Kramer et al. |
| 2006/0135998 A1 | 6/2006 | Libbus et al. |
| 2006/0137698 A1 | 6/2006 | Danek et al. |
| 2006/0142801 A1 | 6/2006 | Demarais et al. |
| 2006/0153876 A1 | 7/2006 | Sanders |
| 2006/0167498 A1 | 7/2006 | DiLorenzo |
| 2006/0178703 A1 | 8/2006 | Huston et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0222667 A1 | 10/2006 | Deem et al. |
| 2006/0225742 A1 | 10/2006 | Deem et al. |
| 2006/0235474 A1 | 10/2006 | Demarais |
| 2006/0241523 A1 | 10/2006 | Sinelnikov et al. |

(56) References Cited

U.S. PATENT DOCUMENTS

| | | |
|---|---|---|
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247683 A1 | 11/2006 | Danek et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276807 A1 | 12/2006 | Keast et al. |
| 2006/0276852 A1 | 12/2006 | Demarais et al. |
| 2006/0278243 A1 | 12/2006 | Danek et al. |
| 2006/0278244 A1 | 12/2006 | Danek et al. |
| 2006/0280772 A1 | 12/2006 | Roschak et al. |
| 2006/0280773 A1 | 12/2006 | Roschak et al. |
| 2006/0282071 A1 | 12/2006 | Utley et al. |
| 2006/0287679 A1 | 12/2006 | Stone |
| 2007/0021803 A1 | 1/2007 | Deem et al. |
| 2007/0025919 A1 | 2/2007 | Deem et al. |
| 2007/0027496 A1 | 2/2007 | Parnis et al. |
| 2007/0032788 A1 | 2/2007 | Edwards et al. |
| 2007/0043342 A1 | 2/2007 | Kleinberger |
| 2007/0043350 A1 | 2/2007 | Soltesz et al. |
| 2007/0055328 A1 | 3/2007 | Mayse et al. |
| 2007/0060954 A1 | 3/2007 | Cameron et al. |
| 2007/0060990 A1 | 3/2007 | Satake |
| 2007/0062545 A1 | 3/2007 | Danek et al. |
| 2007/0066957 A1 | 3/2007 | Demarais et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0083239 A1 | 4/2007 | Demarais et al. |
| 2007/0093802 A1 | 4/2007 | Danek et al. |
| 2007/0093809 A1 | 4/2007 | Edwards et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123922 A1 | 5/2007 | Cooper et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0156185 A1 | 7/2007 | Swanson et al. |
| 2007/0173899 A1 | 7/2007 | Levin et al. |
| 2007/0191902 A1 | 8/2007 | Errico et al. |
| 2007/0197896 A1 | 8/2007 | Moll et al. |
| 2007/0203549 A1 | 8/2007 | Demarais et al. |
| 2007/0225768 A1 | 9/2007 | Dobak, III |
| 2007/0232896 A1 | 10/2007 | Gilboa et al. |
| 2007/0239256 A1 | 10/2007 | Weber et al. |
| 2007/0244479 A1 | 10/2007 | Beatty et al. |
| 2007/0250050 A1 | 10/2007 | Lafontaine |
| 2007/0255270 A1 | 11/2007 | Carney |
| 2007/0255304 A1 | 11/2007 | Roschak et al. |
| 2007/0265639 A1 | 11/2007 | Danek et al. |
| 2007/0265687 A1 | 11/2007 | Deem et al. |
| 2007/0267011 A1 | 11/2007 | Deem et al. |
| 2007/0270794 A1 | 11/2007 | Anderson et al. |
| 2008/0004596 A1 | 1/2008 | Yun et al. |
| 2008/0021274 A1 | 1/2008 | Bayer et al. |
| 2008/0021369 A1 | 1/2008 | Deem et al. |
| 2008/0051839 A1 | 2/2008 | Libbus et al. |
| 2008/0086107 A1 | 4/2008 | Roschak |
| 2008/0091379 A1 | 4/2008 | Lynch et al. |
| 2008/0097422 A1 | 4/2008 | Edwards et al. |
| 2008/0097424 A1 | 4/2008 | Wizeman et al. |
| 2008/0125772 A1 | 5/2008 | Stone et al. |
| 2008/0147137 A1 | 6/2008 | Cohen et al. |
| 2008/0154258 A1 | 6/2008 | Chang et al. |
| 2008/0161801 A1 | 7/2008 | Steinke et al. |
| 2008/0161890 A1 | 7/2008 | Lafontaine |
| 2008/0183248 A1 | 7/2008 | Rezai et al. |
| 2008/0188912 A1 | 8/2008 | Stone et al. |
| 2008/0188913 A1 | 8/2008 | Stone et al. |
| 2008/0194956 A1 | 8/2008 | Aldrich et al. |
| 2008/0208305 A1 | 8/2008 | Rezai et al. |
| 2008/0213331 A1 | 9/2008 | Gelfand et al. |
| 2008/0234564 A1 | 9/2008 | Beatty et al. |
| 2008/0243112 A1 | 10/2008 | De |
| 2008/0255449 A1 | 10/2008 | Warnking et al. |
| 2008/0255642 A1 | 10/2008 | Zarins et al. |
| 2008/0262489 A1 | 10/2008 | Steinke |
| 2008/0275445 A1 | 11/2008 | Kelly et al. |
| 2008/0302359 A1 | 12/2008 | Loomas et al. |
| 2008/0306570 A1 | 12/2008 | Rezai et al. |
| 2008/0312543 A1 | 12/2008 | Laufer et al. |
| 2008/0312725 A1 | 12/2008 | Penner |
| 2008/0319350 A1 | 12/2008 | Wallace et al. |
| 2009/0018473 A1 | 1/2009 | Aldrich et al. |
| 2009/0018538 A1 | 1/2009 | Webster et al. |
| 2009/0030477 A1 | 1/2009 | Jarrard |
| 2009/0036948 A1 | 2/2009 | Levin et al. |
| 2009/0043301 A1 | 2/2009 | Jarrard et al. |
| 2009/0043302 A1 | 2/2009 | Ford et al. |
| 2009/0048593 A1 | 2/2009 | Ganz et al. |
| 2009/0060953 A1 | 3/2009 | Sandars |
| 2009/0062873 A1 | 3/2009 | Wu et al. |
| 2009/0069797 A1 | 3/2009 | Danek et al. |
| 2009/0076409 A1 | 3/2009 | Wu et al. |
| 2009/0076491 A1 | 3/2009 | Roschak et al. |
| 2009/0112203 A1 | 4/2009 | Danek et al. |
| 2009/0124883 A1 | 5/2009 | Wibowo et al. |
| 2009/0131765 A1 | 5/2009 | Roschak et al. |
| 2009/0131928 A1 | 5/2009 | Edwards et al. |
| 2009/0131930 A1 | 5/2009 | Gelbart et al. |
| 2009/0143678 A1 | 6/2009 | Keast et al. |
| 2009/0143705 A1 | 6/2009 | Danek et al. |
| 2009/0143776 A1 | 6/2009 | Danek et al. |
| 2009/0143831 A1 | 6/2009 | Huston et al. |
| 2009/0155336 A1 | 6/2009 | Rezai |
| 2009/0177192 A1 | 7/2009 | Rioux et al. |
| 2009/0192505 A1 | 7/2009 | Askew et al. |
| 2009/0192508 A1 | 7/2009 | Laufer et al. |
| 2009/0204005 A1 | 8/2009 | Keast et al. |
| 2009/0204119 A1 | 8/2009 | Bleich et al. |
| 2009/0221997 A1 | 9/2009 | Arnold et al. |
| 2009/0227885 A1 | 9/2009 | Lowery et al. |
| 2009/0227980 A1 | 9/2009 | Kangas et al. |
| 2009/0232850 A1 | 9/2009 | Manack et al. |
| 2009/0248011 A1 | 10/2009 | Hlavka et al. |
| 2009/0254079 A1 | 10/2009 | Edwards et al. |
| 2009/0254142 A1 | 10/2009 | Edwards et al. |
| 2009/0259274 A1 | 10/2009 | Simon et al. |
| 2009/0264821 A1 | 10/2009 | Mafi et al. |
| 2009/0275840 A1 | 11/2009 | Roschak et al. |
| 2009/0275878 A1 | 11/2009 | Cambier et al. |
| 2009/0281593 A9 | 11/2009 | Errico et al. |
| 2009/0287087 A1 | 11/2009 | Gwerder et al. |
| 2009/0306644 A1 | 12/2009 | Mayse et al. |
| 2009/0318904 A9 | 12/2009 | Cooper et al. |
| 2009/0319002 A1 | 12/2009 | Simon et al. |
| 2010/0003282 A1 | 1/2010 | Deem et al. |
| 2010/0004648 A1 | 1/2010 | Edwards et al. |
| 2010/0010564 A1 | 1/2010 | Simon et al. |
| 2010/0016709 A1 | 1/2010 | Gilboa et al. |
| 2010/0042089 A1 | 2/2010 | Soltesz et al. |
| 2010/0049031 A1 | 2/2010 | Fruland et al. |
| 2010/0049186 A1 | 2/2010 | Ingle et al. |
| 2010/0049188 A1 | 2/2010 | Nelson et al. |

(56) References Cited

U.S. PATENT DOCUMENTS

| | | |
|---|---|---|
| 2010/0057178 A1 | 3/2010 | Simon |
| 2010/0063495 A1 | 3/2010 | Edwards et al. |
| 2010/0070004 A1 | 3/2010 | Hlavka et al. |
| 2010/0076518 A1 | 3/2010 | Hlavka et al. |
| 2010/0087775 A1 | 4/2010 | Deem et al. |
| 2010/0087783 A1 | 4/2010 | Weber et al. |
| 2010/0087809 A1 | 4/2010 | Edwards et al. |
| 2010/0094231 A1 | 4/2010 | Bleich et al. |
| 2010/0114087 A1 | 5/2010 | Edwards et al. |
| 2010/0116279 A9 | 5/2010 | Cooper |
| 2010/0125239 A1 | 5/2010 | Perry et al. |
| 2010/0130892 A1 | 5/2010 | Warnking |
| 2010/0137860 A1 | 6/2010 | Demarais et al. |
| 2010/0145427 A1 | 6/2010 | Gliner et al. |
| 2010/0152835 A1 | 6/2010 | Orr |
| 2010/0160906 A1 | 6/2010 | Jarrard |
| 2010/0160996 A1 | 6/2010 | Simon et al. |
| 2010/0174340 A1 | 7/2010 | Simon |
| 2010/0179424 A1 | 7/2010 | Warnking et al. |
| 2010/0185190 A1 | 7/2010 | Danek et al. |
| 2010/0191089 A1 | 7/2010 | Stebler et al. |
| 2010/0204689 A1 | 8/2010 | Danek et al. |
| 2010/0222851 A1 | 9/2010 | Deem et al. |
| 2010/0228318 A1 | 9/2010 | Errico et al. |
| 2010/0241188 A1 | 9/2010 | Errico et al. |
| 2010/0249873 A1 | 9/2010 | Errico |
| 2010/0256629 A1 | 10/2010 | Wylie et al. |
| 2010/0256630 A1 | 10/2010 | Hamilton, Jr. et al. |
| 2010/0268222 A1 | 10/2010 | Danek et al. |
| 2010/0298905 A1 | 11/2010 | Simon |
| 2010/0305463 A1 | 12/2010 | Macklem et al. |
| 2010/0318020 A1 | 12/2010 | Atanasoska et al. |
| 2010/0331776 A1 | 12/2010 | Salahieh et al. |
| 2011/0004148 A1 | 1/2011 | Ishii |
| 2011/0015548 A1 | 1/2011 | Aldrich et al. |
| 2011/0028898 A1 | 2/2011 | Clark, III et al. |
| 2011/0046432 A1 | 2/2011 | Simon et al. |
| 2011/0060380 A1 | 3/2011 | Gelfand et al. |
| 2011/0079230 A1 | 4/2011 | Danek et al. |
| 2011/0093032 A1 | 4/2011 | Boggs, II et al. |
| 2011/0098762 A1 | 4/2011 | Rezai |
| 2011/0112400 A1 | 5/2011 | Emery et al. |
| 2011/0112521 A1 | 5/2011 | Delonzor et al. |
| 2011/0118725 A1 | 5/2011 | Mayse et al. |
| 2011/0125203 A1 | 5/2011 | Simon et al. |
| 2011/0125213 A1 | 5/2011 | Simon et al. |
| 2011/0130708 A1 | 6/2011 | Perry et al. |
| 2011/0137284 A1 | 6/2011 | Arora et al. |
| 2011/0144630 A1 | 6/2011 | Loeb |
| 2011/0146673 A1 | 6/2011 | Keast et al. |
| 2011/0146674 A1 | 6/2011 | Roschak |
| 2011/0152855 A1 | 6/2011 | Mayse et al. |
| 2011/0152967 A1 | 6/2011 | Simon et al. |
| 2011/0152974 A1 | 6/2011 | Rezai et al. |
| 2011/0166499 A1 | 7/2011 | Demarais et al. |
| 2011/0166565 A1 | 7/2011 | Wizeman et al. |
| 2011/0172655 A1 | 7/2011 | Biggs et al. |
| 2011/0172658 A1 | 7/2011 | Gelbart et al. |
| 2011/0178569 A1 | 7/2011 | Parnis et al. |
| 2011/0184330 A1 | 7/2011 | Laufer et al. |
| 2011/0190569 A1 | 8/2011 | Simon et al. |
| 2011/0195973 A1 | 8/2011 | Johnson |
| 2011/0196288 A1 | 8/2011 | Kaplan et al. |
| 2011/0202098 A1 | 8/2011 | Demarais et al. |
| 2011/0224768 A1 | 9/2011 | Edwards |
| 2011/0230701 A1 | 9/2011 | Simon et al. |
| 2011/0230938 A1 | 9/2011 | Simon et al. |
| 2011/0245756 A1 | 10/2011 | Arora et al. |
| 2011/0251592 A1 | 10/2011 | Biggs et al. |
| 2011/0257622 A1 | 10/2011 | Salahieh et al. |
| 2011/0257647 A1 | 10/2011 | Mayse et al. |
| 2011/0263960 A1 | 10/2011 | Mitchell |
| 2011/0264086 A1 | 10/2011 | Ingle |
| 2011/0270249 A1 | 11/2011 | Utley et al. |
| 2011/0276107 A1 | 11/2011 | Simon et al. |
| 2011/0276112 A1 | 11/2011 | Simon et al. |
| 2011/0282229 A1 | 11/2011 | Danek et al. |
| 2011/0282418 A1 | 11/2011 | Saunders et al. |
| 2011/0301587 A1 | 12/2011 | Deem et al. |
| 2011/0301664 A1 | 12/2011 | Rezai |
| 2011/0301679 A1 | 12/2011 | Rezai et al. |
| 2011/0306851 A1 | 12/2011 | Wang |
| 2011/0306904 A1 | 12/2011 | Jacobson et al. |
| 2011/0306997 A9 | 12/2011 | Roschak et al. |
| 2011/0319958 A1 | 12/2011 | Simon et al. |
| 2012/0004656 A1 | 1/2012 | Jackson et al. |
| 2012/0015019 A1 | 1/2012 | Pacetti et al. |
| 2012/0016256 A1 | 1/2012 | Mabary et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0029500 A1 | 2/2012 | Jenson |
| 2012/0029512 A1 | 2/2012 | Willard et al. |
| 2012/0029591 A1 | 2/2012 | Simon et al. |
| 2012/0029601 A1 | 2/2012 | Simon et al. |
| 2012/0041412 A1 | 2/2012 | Roth et al. |
| 2012/0041509 A1 | 2/2012 | Knudson et al. |
| 2012/0071870 A1 | 3/2012 | Salahieh et al. |
| 2012/0078096 A1 | 3/2012 | Krolik et al. |
| 2012/0083734 A1 | 4/2012 | Ayres et al. |
| 2012/0089078 A1 | 4/2012 | Deem et al. |
| 2012/0089138 A1 | 4/2012 | Edwards et al. |
| 2012/0101326 A1 | 4/2012 | Simon et al. |
| 2012/0101413 A1 | 4/2012 | Beetel et al. |
| 2012/0109278 A1 | 5/2012 | Sih |
| 2012/0111324 A1 | 5/2012 | Kraft et al. |
| 2012/0143132 A1 | 6/2012 | Orlowski |
| 2012/0143177 A1 | 6/2012 | Avitall |
| 2012/0143179 A1 | 6/2012 | Avitall |
| 2012/0143181 A1 | 6/2012 | Demarais et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165803 A1 | 6/2012 | Bencini et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking et al. |
| 2012/0245415 A1 | 9/2012 | Emura et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |
| 2013/0123751 A1 | 5/2013 | Deem et al. |
| 2013/0204068 A1 | 8/2013 | Gnanashanmugam et al. |

(56) References Cited

U.S. PATENT DOCUMENTS

| | | |
|---|---|---|
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0186341 A1 | 7/2014 | Mayse et al. |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2014/0371809 A1 | 12/2014 | Parnis et al. |
| 2015/0051597 A1 | 2/2015 | Mayse et al. |
| 2015/0141985 A1 | 5/2015 | Mayse et al. |
| 2015/0150625 A1 | 6/2015 | Deem et al. |
| 2015/0190193 A1 | 7/2015 | Mayse et al. |
| 2015/0366603 A1 | 12/2015 | Hlavka et al. |
| 2016/0022351 A1 | 1/2016 | Kaveckis et al. |
| 2016/0038725 A1 | 2/2016 | Mayse et al. |
| 2016/0192981 A1 | 7/2016 | Dimmer et al. |
| 2016/0220851 A1 | 8/2016 | Mayse et al. |
| 2016/0278845 A1 | 9/2016 | Mayse |
| 2016/0310210 A1 | 10/2016 | Harshman et al. |
| 2017/0014571 A1 | 1/2017 | Deem et al. |
| 2017/0050008 A1 | 2/2017 | Mayse |
| 2017/0245911 A1 | 8/2017 | Mayse et al. |
| 2018/0028748 A1 | 2/2018 | Deem et al. |
| 2018/0042668 A1 | 2/2018 | Dimmer et al. |
| 2018/0199993 A1 | 7/2018 | Mayse et al. |
| 2019/0083768 A1 | 3/2019 | Deem et al. |
| 2019/0105102 A1 | 4/2019 | Mayse et al. |
| 2019/0142510 A1 | 5/2019 | Mayse et al. |
| 2019/0142511 A1 | 5/2019 | Wahr et al. |
| 2019/0151018 A1 | 5/2019 | Mayse et al. |

FOREIGN PATENT DOCUMENTS

| | | |
|---|---|---|
| CN | 101115448 B | 5/2010 |
| DE | 19529634 A1 | 2/1997 |
| DE | 19952505 A1 | 5/2001 |
| EP | 0189329 A3 | 6/1987 |
| EP | 0286145 A2 | 10/1988 |
| EP | 0280225 A3 | 3/1989 |
| EP | 0282225 B1 | 6/1992 |
| EP | 0643982 A1 | 3/1995 |
| EP | 0908713 A1 | 4/1999 |
| EP | 1143864 A2 | 10/2001 |
| EP | 1271384 A1 | 1/2003 |
| EP | 1281366 A2 | 2/2003 |
| EP | 0908150 B1 | 5/2003 |
| EP | 0768091 B1 | 7/2003 |
| EP | 1326548 A1 | 7/2003 |
| EP | 1326549 A1 | 7/2003 |
| EP | 1400204 A1 | 3/2004 |
| EP | 1297795 B1 | 8/2005 |
| EP | 1588662 A2 | 10/2005 |
| FR | 2659240 B1 | 7/1997 |
| GB | 2233293 A | 1/1991 |
| GB | 2233293 - | 2/1994 |
| JP | S59167707 A | 9/1984 |
| JP | H07289557 A | 11/1995 |
| JP | H0947518 A | 2/1997 |
| JP | H09243837 A | 9/1997 |
| JP | H1026709 A | 1/1998 |
| JP | 2002145784 A | 5/2002 |
| RU | 2053814 C1 | 2/1996 |
| RU | 2091054 C1 | 9/1997 |
| SU | 545358 A1 | 2/1977 |
| WO | WO-8911311 A1 | 11/1989 |
| WO | WO-9301862 A1 | 2/1993 |
| WO | WO-9316632 A1 | 9/1993 |
| WO | WO-9407446 A1 | 4/1994 |
| WO | WO-9501075 A1 | 1/1995 |
| WO | WO-9502370 A2 | 1/1995 |
| WO | WO-9510322 A1 | 4/1995 |
| WO | WO-9519805 A1 | 7/1995 |
| WO | WO-9604860 A1 | 2/1996 |
| WO | WO-9610961 A1 | 4/1996 |
| WO | WO-9725917 A1 | 7/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9818391 A1 | 5/1998 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9932040 A1 | 7/1999 |
| WO | WO-9934831 A1 | 7/1999 |
| WO | WO-9942047 A1 | 8/1999 |
| WO | WO-9964109 A1 | 12/1999 |
| WO | WO-0010598 A2 | 3/2000 |
| WO | WO-0051510 A1 | 9/2000 |
| WO | WO-0062699 A2 | 10/2000 |
| WO | WO-0066017 A1 | 11/2000 |
| WO | WO-0100114 A1 | 1/2001 |
| WO | WO-0103642 A1 | 1/2001 |
| WO | WO-0170114 A1 | 9/2001 |
| WO | WO-0189526 A1 | 11/2001 |
| WO | WO-0205720 A1 | 1/2002 |
| WO | WO-0205868 A2 | 1/2002 |
| WO | WO 0232333 A1 | 4/2002 |
| WO | WO-0232334 A1 | 4/2002 |
| WO | WO-03073358 A2 | 9/2003 |
| WO | WO-03088820 A2 | 10/2003 |
| WO | WO-2004006954 A2 | 1/2004 |
| WO | WO-2004078252 A2 | 9/2004 |
| WO | WO-2004082736 A2 | 9/2004 |
| WO | WO-2004093914 A1 | 11/2004 |
| WO | WO-2004101028 A2 | 11/2004 |
| WO | WO-2005006963 A2 | 1/2005 |
| WO | WO-2005006964 A2 | 1/2005 |
| WO | WO-2005032646 A2 | 4/2005 |
| WO | WO-2005048988 A1 | 6/2005 |
| WO | WO-2006053308 A2 | 5/2006 |
| WO | WO-2006053309 A2 | 5/2006 |
| WO | WO-2006116198 A2 | 11/2006 |
| WO | WO-2004101028 A3 | 12/2006 |
| WO | WO-2007058780 A2 | 5/2007 |
| WO | WO-2007061982 A1 | 5/2007 |
| WO | WO-2007092062 A1 | 8/2007 |
| WO | WO-2007094828 A2 | 8/2007 |
| WO | WO-2007094828 A3 | 11/2007 |
| WO | WO-2007143665 A2 | 12/2007 |
| WO | WO-2008005953 A2 | 1/2008 |
| WO | WO-2008024220 A1 | 2/2008 |
| WO | WO-2008051706 A2 | 5/2008 |
| WO | WO-2008063935 A2 | 5/2008 |
| WO | WO-2009009236 A1 | 1/2009 |
| WO | WO-2009015278 A1 | 1/2009 |
| WO | WO-2009082433 A2 | 7/2009 |
| WO | WO-2007058780 A9 | 10/2009 |
| WO | WO-2009126383 A2 | 10/2009 |
| WO | WO-2009137819 A1 | 11/2009 |
| WO | WO-2009126383 A3 | 12/2009 |
| WO | WO-2010110785 A1 | 9/2010 |
| WO | WO-2011060200 A1 | 5/2011 |

OTHER PUBLICATIONS

Ahnert-Hilger., et al., "Introduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

Amendment After Allowance dated Sep. 17, 2012, in co-pending U.S. Appl. No. 12/372,607, filed Feb. 17, 2009, 12 pages.

An S S., et al., "Airway Smooth Muscle Dynamics; A Common Pathway of Airway Obstruction in Asthma," European Respiratory Journal, 2007, vol. 29 (5), pp. 834-860.

(56) References Cited

OTHER PUBLICATIONS

"Anonymous: Neurotoxin (from Wikipedia)," Retrieved from http://en.wikipedia.org/w/index.php?title=Neurotoxin&printable=yes, Apr. 2, 2015, 23 pages.
Application and File History for U.S. Appl. No. 10/437,882, filed May 13, 2003, Inventor: Mark E. Deem, Apparatus for Treating Asthma Using Neurotoxin.
Application and File History for U.S. Appl. No. 11/445,644, filed Jun. 1, 2006, Inventor: Deem et al., Issued as U.S. Pat. No. 8,172,827 on May 8, 2012.
Application and File History for U.S. Appl. No. 11/446,043, filed Jun. 1, 2006, Inventor: Mark E. Deem, et al., Apparatus for Treating Asthma Using Neurotoxin.
Application and File History for U.S. Appl. No. 11/459,090, filed Jul. 21, 2006, Inventors: Deem et al.
Application and File History for U.S. Appl. No. 12/559,278, filed Sep. 14, 2009, Inventors: Deem et al.
Application and File History for U.S. Appl. No. 13/253,595, filed Oct. 5, 2011, Inventors: Deem et al.
Application and File History for U.S. Appl. No. 13/660,629, filed Oct. 25, 2012, Inventors: Deem et al.
Application and File History for U.S. Appl. No. 13/669,305, filed Nov. 5, 2012, Inventors: Deem et al.
Application and File History for U.S. Appl. No. 15/155,641, filed May 16, 2016, Inventors: Deem et al.
Application and File History for U.S. Appl. No. 14/142,350, filed Dec. 27, 2013, Inventor: Mayse, Methods for Improving Drug Efficacy.
Application and File history for U.S. Appl. No. 14/601,529, filed Jan. 21, 2015, Inventors: Deem et al.
Application and File History for U.S. Appl. No. 15/358,187, filed Nov. 22, 2016, Inventors: Deem et al.
Application and File History for U.S. Appl. No. 14/776,998, filed Sep. 15, 2015, Inventors: Mayse et al.
Application and File History for U.S. Appl. No. 16/036,381, filed Jul. 16, 2018, Inventors: Deem et al.
Babichev., et al., "Clinico-Morphological Comparisons in Patients with Bronchial Asthma after Denervation of the Lungs," Sov Med, 1985, vol. 12, pp. 13-16.
Babichev., et al., "Long-term Results of Surgical Treatment of Bronchial Asthma Based on Adaptive Response," Khirurgiia (Mosk), 1993, vol. 4, pp. 5-11.
Babichev., et al., "Partial Deneration of the Lungs in Bronchial Asthma," Khirurgiia (Mosk), 1985, vol. 4, pp. 31-35.
Barlaw., "Surgical Treatment of Asthma," Postgrad Med. Journal, 1949, vol. 25, pp. 193-196.
Bel E H., "Hot Stuff: Bronchial Thermoplasty for Asthma," American Journal of Respiratory and Critical Care Medicine, 2006, vol. 173, pp. 941-942.
Bester., et al., "Recovery of C-Fiber-Induced Extravasation Following Peripheral Nerve Injury in the Rat," Experimental Neurology, 1998, vol. 154, pp. 628-636.
Bigalke., et al., "Clostridial Neurotoxins," Handbook of Experimental Pharmacology (Aktories, K., and Just, I., eds), 2000, vol. 145, pp. 407-443.
Bittner., et al., "Isolated Light Chains of Botulinum Neurotoxins Inhibit Exocytosis," The Journal of Biological Chemistry, 1989, vol. 264(18), pp. 10354-10360.
Blindt., et al., "Development of a New Biodegradable Intravascular Polymer Stent with Simultaneous Incorporation of Bioactive Substances," The International Journal of Artificial Organs, 1999, vol. 22 (12), pp. 843-853.
Boxem V TJM., et al., "Tissue Effects of Bronchoscopic Electrocautery," Chest, Mar. 2000, vol. 117(3), pp. 887-891.
Bradley., et al., "Effect of Vagotomy on the Breathing Pattern and Exercise Ability in Emphysematous Patients," Clinical Science, 1982, vol. 62, pp. 311-319.
Breekveldt-Postma., et al., "Enhanced Persistence with Tiotropium Compared with Other Respiratory Drugs in COPD," Respiratory Medicine, 2007, vol. 101, pp. 1398-1405.
Brody., et al., "Mucociliary Clearance After Lung Denervation and Bronchial Transection," J Applied Physiology, 1972, vol. 32 (2), pp. 160-164.
Brown R H., et al., "Effect of Bronchial Thermoplasty on Airway Distensibility," European Respiratory Journal, Aug. 2005, vol. 26 (2), pp. 277-282.
Brown R H., et al., "In Vivo Evaluation of the Effectiveness of Bronchial Thermoplasty with Computed Tomography," Journal of Applied Physiology, 2005, vol. 98, pp. 1603-1606.
Buzzi., "Diphtheria Toxin Treatment of Human Advanced Cancer," Cancer Research, 1982, vol. 42, pp. 2054-2058.
Canning., et al., "Reflex Mechanisms in Gastroesophageal Reflux Disease and Asthma," The American Journal of Medicine, 2003, vol. 115 (3A), pp. 45S-48S.
Canning., "Reflex Regulation of Airway Smooth Muscle Tone," J Appl. Physiol, 2006, vol. 101, pp. 971-985.
Castro M., et al., "Effectiveness and Safety of Bronchial Thermoplasty in the Treatment of Severe Asthma: a Multicenter, Randomized, Double-Blind, Sham-Controlled Clinical Trial," American Journal of Respiratory and Critical Care Medicine, 2010, vol. 181, pp. 116-124.
Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.
Chang., "Cell Poration and Cell Fusion Using an Oscillating Electric Field," Biophys. J, 1989, vol. 56 (4), pp. 641-652.
Chernyshova., et al., "The Effect of Low-Energy Laser Radiation in the Infrared Spectrum on Bronchial Patency in Children with Bronchial Asthma," Vopr Kurortol Fizioter Lech Fiz Kult, 1995, vol. 2, pp. 11-14, (6 pages of English translation).
Chhajed P., "Will There be a Role for Bronchoscopic Radiofrequency Ablation," J Bronchol, 2005, vol. 12 (3), p. 184.
Chumakov., et al., "Morphologic Studies of Bronchial Biopsies in Chronic Bronchitis Before and After Treatment," Arkh Patol, 1995, vol. 57 (6), pp. 21-25.(English Abstract and Translation, 8 pages).
Co-pending U.S. Appl. No. 09/095,323, filed Jun. 10, 1998, 26 pages.
Co-pending U.S. Appl. No. 09/244,173, filed Feb. 4, 1999, 74 Pages.
Co-pending U.S. Appl. No. 12/372,607, filed Feb. 17, 2009, 54 pages.
Co-pending U.S. Appl. No. 13/523,223, filed Jun. 14, 2012, 49 pages.
Cox G., et al., "Asthma Control During the Year After Bronchial Thermoplasty," The New England Journal of Medicine, Mar. 29, 2007, vol. 356 (13), pp. 1327-1337.
Cox G., et al., "Bronchial Thermoplasty for Asthma," American Journal of Respiratory and Critical Care Medicine, 2006, vol. 173, pp. 965-969.
Cox G., et al., "Clinical Experience with Bronchial Thermoplasty for the Treatment of Asthma," Chest 124, 2003, p. 106S.
Cox G., et al., "Impact of Bronchial Thermoplasty on Asthma Status: Interim Results From the Air Trial," European Respiratory Society Annual Meeting, Munich, Germany, 2006, 1 page.
Cox G., et al., "Radiofrequency Ablation of Airway Smooth Muscle for Sustained Treatment of Asthma: Preliminary Investigations," European Respiratory Journal, 2004, vol. 24, pp. 659-663.
Crimi., et al., "Protective Effects of Inhaled Ipratropium Bromide on Bronchoconstriction Induced by Adenosine and Methacholine in Asthma," Eur Respir J, 1992, vol. 5, pp. 560-565.
Danek C J., et al., "Reduction in Airway Hyperesponsiveness to Methacholine by the Application of RF Energy in Dogs," J Appl Physiol, 2004, vol. 97, pp. 1946-1953.
De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.
Dierkesmann., et al., "Indication and Results of Endobronchial Laser Therapy," Lung, 1990, vol. 168, pp. 1095-1102.
Dimitrov-Szokodi., et al., "Lung Denervation in the Therapy of Intractable Bronchial Asthma," J. Thoracic Surg, Feb. 1957, vol. 33 (2), pp. 166-184.

(56) References Cited

OTHER PUBLICATIONS

Donohue., et al., "A 6-Month, Placebo-Controlled Study Comparing Lung Function and Health Status Changes in COPD Patients Treated With Tiotropium or Salmeterol," Chest, 2002, vol. 122, pp. 47-55.
European Search Report for Application No. EP06788062, dated Jan. 7, 2014, 9 pages.
"Evis Exera Bronchovideoscope Brochure," Olympus Bf-XT160, Olympus, Jun. 15, 2007, 2 pages.
Extended European Search Report for Application No. EP04752282, dated Feb. 23, 2011, 5 pages.
Communication for European Application No. EP04752282, dated Aug. 8, 2018, 5 pages.
Feshenko., et al., "Clinico-Morphological Comparisons in the Laser Therapy of Chronic Bronchitis Patients," Lik Sprava, 1993, vol. 10-12, pp. 75-79.(English abstract, 1 Page).
Friedman., et al., "Healthcare Costs with Tiotropium Plus Usual Care versus Usual Care Alone Following 1 Year of Treatment in Patients with Chronic Obstructive Pulmonary Disorder (COPD)," Pharmacoeconomics, 2004, vol. 22 (11), pp. 741-749.
Gaude., G.S., "Pulmonary Manifestations of Gastroesophageal Reflux Disease," Annals of Thoracic Medicine, Jul.-Sep. 2009, vol. 4 (3), pp. 115-123.
Gelb., et al., "Laser in Treatment of Lung Cancer," American College of Chest Physicians, Nov. 1984, vol. 86 (5), pp. 662-666.
George., et al., "Factors Associated With Medication Nonadherence in Patients With COPD," Chest, 2005, vol. 128, pp. 3198-3204.
Gerasin., et al., "Endobronchial Electrosurgery," Chest, 1988, vol. 93, pp. 270-274.
Gibson., et al., "Gastroesophageal Reflux Treatment for Asthma in Adults and Children," Cochrane Database Syst. Rev. 2:CD001496, 2003. (Abstract only).
Glanville., et al., "Bronchial Responsiveness after Human Heart-Lung Transplantation," Chest, 1990, vol. 97 (6), pp. 1360-1366.
Glanville., et al., "Bronchial Responsiveness to Exercise after Human Cardiopulmonary Transplantation," Chest, 1989, vol. 96 (2), pp. 281-286.
"Global Strategy for Asthma Management and Prevention," 2002, 192 pages.
Gosens., et al., "Muscarinic Receptor Signaling in the Pathophysiology of Asthma and COPD," Respiratory Research, 2006, vol. 7 (73), pp. 1-15.
Groeben., et al., "High Thoracic Epidural Anesthesia Does Not Alter Airway Resistance and Attenuates the Response to an Inhalational Provocation Test in Patients with Bronchial Hyperreactivity," Anesthesiology, 1994, vol. 81 (4), pp. 868-874.
Guarini., et al., "Efferent Vagal Fibre Stimulation Blunts Nuclear Factor-kB Activation and Protects Against Hypovolemic Hemmorrhagic Shock," Circulation, 2003, vol. 107, pp. 1189-1194.
Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.
Guzman H.R, et al., "Equilibrium Loading of Cells with Macromolecules by Ultrasound: Effects of Molecular Size and Acoustic Energy," J Pharm Sci., Jul. 2002, vol. 91 (7), pp. 1693-1701.
Hainsworth., et al., "Afferent Lung Denervation by Brief Inhalation of Steam," Journal of Applied Physiology, May 1972, vol. 34 (5), pp. 708-714.
Harding., "Pulmonary Manifestations of GERD: Pathophysiology and Management," Division of Pulmonary, Allergy, and Critical Care Medicine—University of Alabama at Birmingham: 4 pages.
Harding., "Recent Clinical Investigations Examining the Association of Asthma and Gastroesophageal Reflux," The American Journal of Medicine, 2003, vol. 115 (Suppl 3A), pp. 39S-44S. (Abstract only).
Hiraga., "Experimental surgical therapy of bronchial asthma. The effect of denervation in dogs," Nihon Kyobu Shikkan Gakkai Zasshi, 1981, vol. 19 (1), pp. 46-56.
Hoffmann., et al., "Inhibition of Histamine-Induced Bronchoconstriction in Guinea Pig and Swine by Pulsed Electrical Vagus Nerve Stimulation," Neuromodulation: Technology at the Neural Interface, 2009, pp. 1-9.
Hooper., et al., "Endobronchial Electrocautery," Chest, 1985, vol. 87 (6), pp. 712-714.
International Search Report and Written Opinion for Application No. PCT/US2006/028310, dated Aug. 8, 2007, 7 pages.
International Search Report and Written Opinion for Application No. PCT/US2014/028063, dated Aug. 27, 2014, 24 pages.
International Search Report for Application No. PCT/US2004/015222, dated Oct. 5, 2006, 3 pages.
Ivanyuta O M., et al., "Effect of Low-Power Laser Irradiation of Bronchia Mucosa on the State of Systemic and Local Immunity in Patients with Chronic Bronchitis," Problemy Tuberkuleza, 1991, vol. 6, pp. 26-29.
James., et al., "The Mechanics of Airway Narrowing in Asthma," The American Review of Respiratory Disease, 1989, vol. 139, pp. 242-246.
Jammes., et al., "Assessment of the Pulmonary Origin of Bronchoconstrictor Vagal Tone," The Journal of physiology, 1979, vol. 291, pp. 305-316.
Janssen L. J., "Asthma therapy: how far have we come, why did we fail and where should we go next?," European Respiratory Journal, 2009, vol. 33, pp. 11-20.
Jiang., et al., "Effects of Antireflux Treatment on Bronchial Hyperresponsiveness and Lung Function in Asthmatic Patients with Gastroesophageal Reflux Disease," World Journal of Gastroenterology, 2003, vol. 9, pp. 1123-1125. (Abstract only).
Khmel'Kova et al., "Does laser irridation affect bronchial obstruction?," Probl Tuberk, 1995, vol. 3, pp. 41-42 (Abstract only).
Khoshoo., et al., "Role of Gastroesophageal Reflux in Older Children with Persistent Asthma," Chest, 2003, vol. 123, pp. 1008-1013. (Abstract only).
Kiljander., "The Role of Proton Pump Inhibitors in the Management of Gastroesophageal Reflux Disease-Related Asthma and Chronic Cough," The American Journal of Medicine, 2003, vol. 115 (Suppl 3A), pp. 65S-71S. (Abstract only.).
Kistner., et al., "Reductive Cleavage of Tetanus Toxin and Botulinum Neurotoxin A by the Thioredoxin System from Brain," Naunyn-Schmiedebergs Arch Pharmacal, Feb. 1992, vol. 345 (2), pp. 227-234.
Kitamura S., "Color Atlas of Clinical Application of Fiberoptic Bronchoscopy," 1990, Year Book Medical Publishers, p. 17.
Kletskin., et al., "Value of Assessing the Autonomic Nervous System in Bronchial Asthma in Selecting the Surgical Treatment Method," Khirurgiia (Mosk), 1987, vol. 7, pp. 91-95.
Kliachkin., et al., "Bronchoscopy in the Treatment of Bronchial Asthma of Infectious Allergic Origin," Terapevticheskiĭ arkhiv, 1982, vol. 54 (4), pp. 76-79.
Korochkin., et al., "Use of a Helium-Neon Laser in Combined Treatment of Bronchial Asthma," New Developments in Diagnostics and Treatment, 1990, 9 pages.
Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.
Kozaki., et al., "New Surgical Treatment of Bronchial Asthma—Denervation of the Hilus Pulmonis (2)," Nippon Kyobu Geka Gakkai Zasshi, 1974, vol. 22 (5), pp. 465-466.
Kraft M., "The Distal Airways: Are they Important in Asthma?," European Respiratory, 1999, pp. 1403-1417.
Kreitman., "Taming Ricin Toxin," Nature Biotechnology, 2003, vol. 21, pp. 372-374.
Kuntz., "The Autonomic Nervous System in Relation to the Thoracic Viscera," Chest, 1944, vol. 10, pp. 1-18.
Lennerz., et al., "Electrophysiological Characterization of Vagal Afferents Relevant to Mucosal Nociception in the Rat Upper Oesophagus," The Journal of physiology, 2007, vol. 582 (1), pp. 229-242.
Levin., "The Treatment of Bronchial Asthma by Dorsal Sympathectomy," Annals of Surgery, 1935, vol. 102 (2), pp. 161-170.

(56) References Cited

OTHER PUBLICATIONS

Lim E E., et al., "Botulinum Toxin: A Novel Therapeutic Option for Bronchial Asthma?," Medical Hypotheses, 2006, vol. 66, pp. 915-919.
Liou., et al., "Causative and Contributive Factors to Asthmas Severity and Patterns of Medication Use in Patients Seeking Specialized Asthma Care," Chest, 2003, vol. 124, pp. 1781-1788. (Abstract only).
Lokke., et al., "Developing COPD: A 25 Year Follow Up Study of the General Population," Thorax, 2006, vol. 61, pp. 935-939.
Macklem P T., "Mechanical Factors Determining Maximum Bronchoconstriction, European Respiratory Journal," Jun. 1989, vol. 6, pp. 516s-519s.
Maesen., et al., "Tiotropium Bromide, A New Long-Acting Antimuscarinic Bronchodilator: A Pharmacodynamic Study in Patients with Chronic Obstructive Pulmonary Disease (COPD)," The European Respiratory Journal, 1995, vol. 8, pp. 1506-1513.
Magnussen., et al., "Effect of Inhaled Ipratropium Bromide on the Airway Response to Methacholine, Histamine, and Exercise in Patients with Mild Bronchial Asthma," Respiration, 1992, vol. 59, pp. 42-47. 0.
Maltais., et al., "Improvements in Symptom-Limited Exercise Performance Over 8 h With Once-Daily Tiotropium in Patients With COPD," Chest, 2005, vol. 128, pp. 1168-1178.
Martin N., et al., "Bronchial Thermoplasty for the Treatment of Asthma," Current Allergy and Asthma Reports, Jan. 2009, vol. 9 (1), pp. 88-95.
Mathew., et al., "Gastro-Oesophageal Reflux and Bronchial Asthma: Current Status and Future Directions," Postgraduate Medical Journal, 2004, vol. 80, pp. 701-705.
Mayse M., et al., "Clinical Pearls for Bronchial Thermoplasty," J Bronchol, Apr. 2007, vol. 14 (2), pp. 115-123.
McEvoy C E., et al., "Changing the Landscape: Bronchial Thermoplasty Offers a Novel Approach to Asthma Treatment," Advance for Managers of Respiratory Care, Oct. 24-25, 2007, pp. 22 - 25.
McKay., et al., "Autocrine Regulation of Asthmatic Airway Inflammation: Role of Airway Smooth Muscle," Respiratory Research, 2002, vol. 3 (11), pp. 1-13.
Mehta., et al., "Effect of Endobronchial Radiation therapy on Malignant Bronchial Obstruction," Chest, Mar. 1990, vol. 97 (3), pp. 662-665.
Merriam-Webster.com, "Medication," Merriam-Webster, n.d.Web, Jul. 20, 2017, 10 pages.
Meshalkin., et al., "Partial Denervation of the Pulmonary Hilus as One of the Methods of Surgical Treatment of Bronchial Asthma," Grudnaia Khirurgiia, 1975, vol. 1, pp. 109-111.
Michaud G., et al., "Positioned for Success: Interest in Diagnostic and Therapeutic Bronchoscopy is Growing," Advance for Managers of Respiratory Care, Jul.-Aug. 2008, pp. 40, 42-43.
Miller J D., et al., "A Prospective Feasibility Study of Bronchial Thermoplasty in the Human Airway," 2005, vol. 127 (6), pp. 1999-2006.
Montaudon M., et al., "Assessment of Bronchial Wall Thickness and Lumen Diameter in Human Adults Using Multi-Detector Computed Tomography: Comparison with Theoretical Models," Journal of Anatomy, 2007, vol. 211, pp. 579-588.
Moore K.L., "Clinically Oriented Anatomy," Williams & Wilkins, Baltimore, 1985, 2nd edition, pp. 85 and 87(Abstract only).
Netter F H., "The Ciba Collection of Medical Illustrations," Respiratory System, CIBA-GEIGY Corporation, West Caldwell, 1979, vol. 7, p. 23, section 1. (Abstract only).
Non-Final Office Action dated Apr. 27, 2010 for U.S. Appl. No. 11/398,353, filed Apr. 4, 2006, 8 pages.
Non-Final Office Action dated Aug. 31, 2009 for U.S. Appl. No. 11/398,353, filed Apr. 4, 2006, 7 pages.
Notice of final Rejection dated Sep. 2, 2008 for Japanese Patent Application No. 2000-553172, filed Jun. 9, 1999, 5 pages.

O'Connor., et al., "Prolonged Effect of Tiotropium Bromide on Methacholine-induced Bronchoconstriction in Asthma," American Journal of Respiratory and Critical Care Medicine, 1996, vol. 154, pp. 876-880.
Office Action dated Mar. 12, 2015 for Chinese Application No. 2011104106059.0 filed May 13, 2004, 10 pages.
Office Action dated May 24, 2016 for Japanese Application No. JP2015-020827 filed Jun. 16, 2015, 7 pages.
Office Action dated Aug. 21, 2017 for Japanese Application No. 2016-227703 filed Nov. 24, 2016, 4 pages.
O'Sullivan M P., et al., "Apoptosis in the Airways: Another Balancing Act in the Epithelial Program," American Journal of Respiratory Cell and Molecular Biology, 2003, vol. 29, pp. 3-7.
Ovcharenko., et al., "Endobronchial Use of Low-Frequency Ultrasound and Ultraviolet Laser Radiation in the Complex Treatment of Patients With Suppurative Bronchial Diseases," Problemy Tuberkuleza, 1997, vol. 3, pp. 40-42. (Abstract only).
Overholt., "Glomectomy for Asthma," Diseases of the Chest, 1961, vol. 40, pp. 605-610.
Pavord I D., et al., "Safety and Efficacy of Bronchial Thermoplasty in Symptomatic, Severe Asthma," American Journal of Respiratory and Critical Care Medicine, 2007, vol. 176, pp. 1185-1191.
PCT International Search Report for Application No. PCT/US00/05412, dated Jun. 20, 2000, 2 pages.
PCT International Search Report for Application No. PCT/US00/18197, dated Oct. 3, 2000, 1 page.
PCT International Search Report for Application No. PCT/US00/28745, dated Mar. 28, 2001, 6 pages.
PCT International Search Report for Application No. PCT/US98/03759, dated Jul. 30, 1998, 1 page.
Peter K. Jeffery, "Remodeling in Asthma and Chronic Obstructive Lung Disease," American Journal of Respiratory and Critical Care Medicine, 2001, vol. 164 (10), pp. S28-S38.
Peters, et al., "Tiotropium Bromide Step-Up Therapy for Adults with Uncontrolled Asthma," New England Journal of Medicine, Oct. 28, 2010, vol. 363 (18), pp. 1715-1726.
Petrou et al., "Bronchoscopic Diathermy Resection and Stent Insertion: a Cost Effective Treatment for Tracheobronchial Obstruction," Thorax, 1993, vol. 48, pp. 1156-1159.
Polosukhin., "Dynamics of the Ultrastructural Changes in Blood and Lymphatic Capillaries of Bronchi in Inflammation and Following Endobronchial Laser Therapy," Virchows Arch, 1997, vol. 431, pp. 283-290.
Polosukhin., "Regeneration of Bronchial Epithelium of Chronic Inflammatory Changes Under Laser Treatment," Pathology, Research and Practice, 1996, vol. 192 (9), pp. 909-918.
Polosukhin., "Ultrastructural Study of the Destructive and Repair Processes in Pulmonary Inflammation and Following Endobronchial Laser Therapy," Virchows Arch, 1999, vol. 435, pp. 13-19.
Polosukhin., "Ultrastructure of the Blood and Lymphatic Capillaries of the Respiratory Tissue During Inflammation and Endobronchial Laser Therapy," Ultrastructural Pathology, 2000, vol. 24, pp. 183-189.
Preliminary Amendment and Response to Restriction Requirement dated Oct. 22, 2012, for U.S. Appl. No. 13/523, 223, filed Jun. 14, 2012.
Provotorov V M., et al., "Clinical Efficacy of Treatment of Patients with Non-Specific Pulmonary Diseases by Using Low-Power Laser Irradiation and Performing Intrapulmonary Drug Administration," Terapevichesky Arkhiv, 1991, vol. 62, pp. 18-23.
Provotorov V.M., et al., "The Clinical Efficacy of Treating Patients with Nonspecific Lung Disease by Using Low-energy Laser Irradiation and Intrapulmonary Drug Administration," ISSN: 0040-3660, Terapevticheskii Arkhiv (USSR), 1991, vol. 62 (12), pp. 18-23 (11 pages).
Raj., "Editorial," Pain Practice, 2004, vol. 4 (1S), pp. S1-S3.
Ramirez et al., "Sympathetomy in Bronchial Asthma," J. A. M. A., 1925, vol. 84 (26), pp. 2002-2003.
Rienhoff., et al., "Treatment of Intractable Bronchial Asthma by Bilateral Resection of the Posterior Pulmonary Plexus," Arch Surg, 1938, vol. 37 (3), pp. 456-469.
Rocha-Singh K J., "Renal Artery Denervation: A Brave New Frontier," Endovascular Today, Feb. 2012, pp. 45-53.

(56) References Cited

OTHER PUBLICATIONS

Rubin., et al., "Bronchial Thermoplasty Improves Asthma Status of Moderate to Severe Persistent Asthmatics Over and Above Current Standard-of-Care," American College of Chest Physicians, 2006, 2 pages.
Savchenko., et al., "Adaptation of Regulatory Physiological Systems in Surgical Treatment of Patients with Bronchial Asthma," Klin Med (Mask), 1996, vol. 74 (7), pp. 38-39.
Schmitt G.S., et al., "Indwelling Transbronchial Catheter Drainage of Pulmonary Abscess," Ann Thorac Surg, Jan. 1988, vol. 45 (1), pp. 43-47.
Sengupta., "Part 1 Oral Cavity, Pharynx and Esophagus—Esophageal Sensory Physiology," GI Motility online, 2006, 17 pages.
Seow C Y., et al., "Signal Transduction in Smooth Muscle Historical Perspective on Airway Smooth Muscle: The Saga of a Frustrated Cell," Journal of applied physiology, 2001, vol. 91, pp. 938-952.
Sepulveda., et al., "Treatment of Asthmatic Bronchoconstriction by Percutaneous Low Voltage Vagal Nerve Stimulation: Case Report," Internet Journal of Asthma, Allergy, and Immunology, 2009, vol. 7 (2), 3 pages.
Shaari., et al., "Rhinorrhea is Decreased in Dogs After Nasal Application of Botulinum Toxin," Otolaryngol Head Neck Surgery, Apr. 1995, vol. 112 (4), pp. 566-571.
Sheski F D., et al., "Cryotherapy, Electrocautery, and Brachytherapy," Clinics in Chest Medicine, Mar. 1999, vol. 20 (1), pp. 123-138.
Shesterina M V., et al., "Effect of laser therapy on immunity in patients with bronchial asthma and pulmonary tuberculosis," 1993, pp. 23-26.
Sil'Vestrov., et al., "The Clinico-Pathogenetic Validation and Efficacy of the Use of Low-Energy Laser Irradiation and Glucocorticoids in the Treatment of Bronchial Patients," Department of Therapy of the Pediatric and Stomatological Faculties of the N.N. Burdenko Voronezh Medical Institute, vol. 63(11), 1991, pp. 87-92.
Simonsson., et al., "Role of Autonomic Nervous System and the Cough Reflex in the Increased Responsiveness of Airways in Patients with Obstructive Airway Disease," The Journal of Clinical Investigation, 1967, vol. 46 (11), pp. 1812-1818.
Simpson., et al., "Isolation and Characterization of the botulinum Neurotoxins," Methods Enzymol, 1988, vol. 165, pp. 76-85/
Simpson L.L., "The Origin, Structure, and Pharmacological Activity of Botulinum Toxin," Pharmacol Reviews, Sep. 1981, vol. 33 (3), pp. 155-188.
Solway J., et al., "Airway Smooth Muscle as a Target for Asthma Therapy," The New England Journal of Medicine, Mar. 29, 2007, vol. 356 (13), pp. 1367-1369.
Sontag., et al., "Asthmatics with Gastroesophageal Reflux: Long-term Results of a Randomized Trial of Medical and Surgical Antireflux Therapies," The American Journal of Gastroenterology, 2003, vol. 98, pp. 987-999. (Abstract only.).
International Preliminary Report on Patentability No. PCT/US2014/028063, dated Sep. 24, 2015, 20 pages.
International Preliminary Report on Patentability for Application No. PCT/US2006/028310, dated Jan. 22, 2008, 7 pages.
Stein., "Possible Mechanisms of Influence of Esophageal Acid on Airway Hyperresponsiveness," The American Journal of Medicine, 2003, vol. 115 (Suppl 3A), pp. 55S-59S. (Abstract only.).
Sterk P J., "Heterogeneity of Airway Hyperresponsiveness: Time for Unconventional, but Traditional Studies," The American Pshychoiogical Society, 2004, pp. 2017-2018.
Sundaram, et al., "An Experimental and Theoretical Analysis of Ultrasound-Induced Permeabilization of Cell Membranes," Biophysical Journal, May 2003, vol. 84 (5), pp. 3087-3101.
Takino., et al., "Surgical Removal of the Carotid Body and its Relation to the Carotid Chemoreceptor and Baroreceptor Reflex in Asthmatics," Dis Chest, 1965, vol. 47, pp. 129-138.
Tashkin., et al., "Long-term Treatment Benefits With Tiotropium in COPD Patients With and Without Short-term Bronchodilator Responses," Chest, 2003, vol. 123, pp. 1441-1449.
Toma T P., "Brave New World for Interventional Bronchoscopy," Thorax, 2005, vol. 60, pp. 180-181.
Trow T., "Clinical Year in Review I, proceedings of the American Thoracic Society," 2006, vol. 3, pp. 553-556.
Tschumperlin D J., et al., "Chronic Effects of Mechanical Force on Airways," Annual Review of Physiology, 2006, vol. 68, pp. 563-583.
Tschumperlin D J., et al., "Mechanical Stimuli to Airway Remodeling," American Journal Respiratory and Critical Care Medicine, 2001, vol. 164, pp. S90-S94.
Tsugeno., et al., "A Proton-Pump Inhibitor, Rabeprazole, Improves Ventilatory Function in Patients with Asthma Associated with Gastroesophageal Reflux," Scand J Gastroenterol, 2003, vol. (38), pp. 456-461. (Abstract only).
Tsuji., et al., "Biodegradable Stents as a Platform to Drug Loading," International Journal of Cardiovascular Interventions, 2003, vol. 5(1), pp. 13-16.
Unal., et al., "Effect of Botulinum Toxin Type A on Nasal Symptoms in Patients with Allergic Rhinitis: A Double-blind, Placebo-controlled Clinical Trial," Acta Oto-Laryngologica, Dec. 2003, vol. 123 (9), pp. 1060-1063.
UNSW, "Embryo-Respiratory System," Embryology, 2007, retrieved from: http://embryology.med.unsw.edu.au/Refer/respire/select.htm on Dec. 10, 2007, 22 pages.
Urologix inc., "Cooled ThermoTherapy™" retrieved on Mar. 5, 2013, from http://www.urologix.com/cliinicians/cooled-thermotherapy.php, 2012, 2 pages.
Urologix, Inc, "CTC Advance.TM. Instructions for Use," Targis. RTM. System Manual, 2010, 8 pages.
Velden V D., et al., "Autonomic Innervation of Human Airways: Structure, Function, and Pathophysiology in Asthma," Neuroimmunomodulation, 1999, vol. 6, pp. 145-159.
Verhein., et al., "Neural Control of Airway Inflammation," Current Allergy and Asthma Reports, 2009, vol. 9, pp. 484-490.
Vincken., et al., "Improved health outcomes in patients with COPD during 1 yr's treatment with tiotropium," Eur. Respir. J., 2002, vol. 19, pp. 209-216.
Vorotnev., et al., "Treatment of Patients with Chronic Obstructive Bronchitis Using Low Energy Laser at a General Rehabilitation Center," Therapeutic Archive, 1997, vol. 3, pp. 17-19.
Wagner., et al., "Methacholine causes reflex bronchoconstriction," J. Appi. Physiol, 1999, vol. 86, pp. 294-297.
Wahidi., et al., "State of the Art: Interventional Pulmonology," American College of Chest Physicians, Jan. 2007, vol. 131 (1), pp. 261-274.
Weaver, "Electroporation: A General Phenomenon for Manipulating Cells and Tissues," Journal of Cellular Biochemistry, Apr. 1993, vol. 51(4), pp. 426-435.
Wechsler M E., "Bronchial Thermoplasty for Asthma: A Critical Review of a New Therapy," Allergy and Asthma Proceedings, Jul.-Aug. 2008, vol. 29 (4), pp. 1-6.
Wiggs B R., et al., On the Mechanism of Mucosal Folding in Normal and Asthmatic Airways, J. Appl. Physiol, Dec. 1997, vol. 83 (6), pp. 1814-1821.
Wilson K C., et al., "Flexible Bronchoscopy: Indications and contraindications," UptoDate, Nov. 12, 2010 (retrieved Sep. 30, 2012 from www.uptodate.com), 15 pages.
Wilson S R., et al., "Global assessment after bronchial thermoplasty: the patient's perspective," Journal of Outcomes Research, 2006, vol. 10, pp. 37-46.
Wirtz., et al., "Bilateral Lung Transplantation for Severe Persistent and Difficult Asthma," The Journal of Heart and Lung Transplantation, 2005, vol. 24 (10), pp. 1700-1703.

\* cited by examiner

APPARATUS FOR TREATING ASTHMA USING NEUROTOXIN

RELATED APPLICATIONS

This application is a division of application Ser. No. 15/155,641 filed May 16, 2016, which in turn is a continuation of application Ser. No. 13/669,305 filed Nov. 5, 2012, now U.S. Pat. No. 9,339,618 issued May 17, 2016, which in turn is a continuation of application Ser. No. 11/446,043 filed Jun. 1, 2006, now abandoned, which in turn is a continuation of application Ser. No. 10/437,882 filed May 13, 2003, now abandoned, each of which is hereby fully incorporated herein by reference.

BACKGROUND OF THE INVENTION

Field of the Invention

The present invention relates to apparatus for treating asthma by controlled delivery of neurotoxin 5 using a neurotoxin applicator assembly.

The lung is made up of progressively smaller bronchial bifurcations stemming downward from the trachea. The trachea and proximal bronchi are lumens consisting of an outer layer of fascia surrounding a U-shaped inner cartilaginous layer, wherein the open portion of the U is spanned by smooth muscle. Inside the cartilaginous layer are a collagenous elastic layer and an innermost epithelial layer. Mucus secreting goblet cells and transport cilial cells are interspersed within these inner layers.

As the bronchi branch and get smaller, the cartilaginous layer changes from a U-shape to irregular and helical shapes. In addition, the smooth muscle layer becomes helical bands surrounding the entire circumference of the bronchi, the goblet cells gradually decrease in numbers and the ciliated cells get smaller and fewer in number. In the most distal bronchi, the outer cartilaginous layer disappears completely, the smooth muscle layer becomes the outermost layer and goblet cells and ciliated cells disappear completely.

Asthma is a complex disease of the bronchial tree, characterized by airway hyperresponsiveness to allergens, stress and environmental triggers. Environmental triggers include irritants such as pollutants and non-allergenic triggers such as exposure to cold air. Airway hyperresponsiveness results in acute narrowing of the entire bronchial tree reducing airflow through the lungs, compromising respiration and limiting gas exchange in the alveoli. The narrowing of the bronchial tree is a result of three basic characteristic physiologic responses: (1) smooth muscle contraction; (2) increased mucus production; and (3) edema caused by arterial dilatation and increased arterial permeability. The triggering mechanisms for these physiologic responses are part of the body's inflammatory response system.

Chronic uncontrolled asthma can result in structural changes to the bronchial wall itself. Smooth muscle hyperplasia results in thickening of the smooth muscle components of the bronchial wall. Thickening of the subepithelial collagen layer that lies between the airway epithelium and the smooth muscle layer results in progressive stiffening of the wall of the bronchi. Studies have shown that stiffening of the airway wall results in more profound narrowing of the airway for a given asthma attack. This is due to changes in the ability of the mucosal layer to fold in response to the smooth muscle layer contraction.

Recently, the controlled injection of neurotoxin has become a common procedure for controlling skeletal muscle spasms. A frequently used neurotoxin for this procedure is the botulinum toxin, serotype A, sold commercially by Allergan, Inc. as BOTOX®. BOTOX® neurotoxin blocks the release of neurotransmitter from the nerves that control the contraction of the target muscles. Many applications for BOTOX® neurotoxin have been proposed and/or clinically tested, including cervical dystonia, cosmetic relief of frown lines and tremor associated with cerebral palsy. Recently, BOTOX® neurotoxin has become the subject of clinical study for the relief of hyperhidrosis (profuse sweating) and hypersalivation. These studies indicate that BOTOX® neurotoxin can be used to control the action of cholinergic parasympathetic nerves as well as large skeletal muscle groups. The recent findings open the possibility of using neurotoxins such as BOTOX® neurotoxin to control some of the main mechanisms of airway narrowing in asthmatic attacks, specifically smooth muscle contraction and hypersecretion of mucus from the goblet cells. Additionally, there is evidence that some part of the inflammatory response of asthma is stimulated by the release of the neurotransmitters which BOTOX® neurotoxin inhibits. This opens the possibility that BOTOX® neurotoxin may also work to mitigate the inflammatory cycle itself.

The use of neurotoxin for the control of asthma is described in U.S. Pat. No. 6,063,768 to First, wherein asthma is included in a list of neurogenic inflammatory disorders that may be controlled through the action of neurotoxins such as BOTOX® neurotoxin. That patent also describes that BOTOX® neurotoxin could be aerosolized and introduced into the lungs. An earlier patent, U.S. Pat. No. 5,766,605 to Sanders, et al. describes the use of BOTOX® neurotoxin to treat asthma and COPD, but does not describe the methods or devices used to do so. Further mention of BOTOX® neurotoxin in connection with asthma is provided in a press release dated Feb. 7, 2003 by the University of Alberta in describing the work of Dr. Redwan Moqbel. The release mentions that Dr. Moqbel and others are researching the possible use of neurotoxins such as tetanus and botulinum toxin to prevent eosinophils from activating and starting the inflammatory cascade that results in an asthma attack.

While it may be possible to simply aerosolize neurotoxins for introduction into the lungs, introducing it into the patient through traditional inhalation means would expose the mouth, tongue, epiglottis, vocal cords, etc. to the actions of the neurotoxin, with obvious deleterious results. Much more controlled and direct application of the neurotoxin to the desired tissue is required for safe and effective therapy.

Accordingly, it would be desirable to provide apparatus that enables controlled delivery of a neurotoxin to target treatment areas within a patient's bronchial airways.

It also would be desirable to provide an apparatus permitting the controlled injection of neurotoxin into the bronchial wall of a patient.

It would further be desirable to provide a needle-less injection apparatus to eliminate potential complications related to the presence of needles within a patient's bronchial airways.

Additionally, it would be desirable to provide an apparatus permitting the application of neurotoxin onto a target treatment area within a patient's bronchial airways.

BRIEF SUMMARY OF THE INVENTION

In view of the foregoing, it is an object of the present invention to provide apparatus that enables the controlled delivery of a neurotoxin to target treatment areas within a patient's bronchial airways.

It is a further object of the present invention to provide an apparatus permitting the controlled injection of neurotoxin into the bronchial wall of a-patient.

It is an additional object of the present invention to provide a needle-less injection apparatus to eliminate potential complications related to the presence of needles within a patient's bronchial airways.

It is another object of the present invention to provide an apparatus permitting the application of neurotoxin onto a target treatment area within a patient's bronchial airways.

These and other objects of the present invention are accomplished by providing an intrabronchial neurotoxin delivery system for controlled delivery of neurotoxin to a target treatment area within a patient's bronchial airways to lessen the effects of asthma. The introduction of neurotoxin into the bronchial airways disables the hyperresponsive smooth muscle layer and controls the hypersecretion of mucus.

The intrabronchial neurotoxin delivery system preferably includes a bronchoscope and neurotoxin applicator assembly. The neurotoxin applicator assembly may be a needle assembly, rotating needle assembly, needle-less injection assembly or a nebulizer assembly.

In a first illustrative embodiment, the neurotoxin applicator assembly comprises a needle assembly including at least one needle having a lumen in fluid communication with a source of liquid neurotoxin. The needles are preformed to contract radially when disposed within a lumen, such as a lumen of the bronchoscope, but may be extended to penetrate and inject small doses of neurotoxin into the bronchial wall of a patient.

In an alternative embodiment, the neurotoxin applicator assembly comprises a rotating needle assembly including plural needles disposed along the circumference of a wheel. Again, the needles include lumens in fluid communication with a source of liquid neurotoxin. In operation, the wheel is adapted to be rolled across a target treatment area about a central hub. Optionally, the rotating needle assembly may include a fender to protect a portion of the bronchial wall substantially opposite the target treatment area.

In another alternative embodiment, the neurotoxin applicator assembly comprises a needle-less injection assembly including a shaft having at least one port in fluid communication with a source of liquid neurotoxin. The needle-less injection assembly can be used to inject neurotoxin into the bronchial wall without needle penetration. Optionally, an inflatable balloon may be provided to help position the at least one port adjacent the target treatment area.

In yet a further alternative embodiment, the neurotoxin applicator assembly comprises a nebulizer assembly including an atomizer in fluid communication with a source of liquid neurotoxin. The atomizer converts the liquid neurotoxin into a fine spray or mist that is directed onto the target treatment area. The particle size of the mix can be controlled using injection pressure or atomizer head design to access specific portions of the lung adjacent to or downstream of the treatment device. An inflatable balloon optionally may be provided to facilitate positioning the atomizer adjacent the target treatment area. The balloon also serves to isolate the lung segment downstream of the device to prevent reflux of the mist into undesired portions of the airway. In addition, lumens optionally may be disposed between the balloon and atomizer to provide a ventilation system that allows pressure control of the treatment area to prevent over-inflation of the lung, mixing of the atomized fluid, and evacuation of remaining mist at termination of therapy, prior to balloon deflation.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 9AA is a cross-sectional view taken along line 9AA-9AA in FIG. 9A.

DETAILED DESCRIPTION OF THE INVENTION

Figure 1:
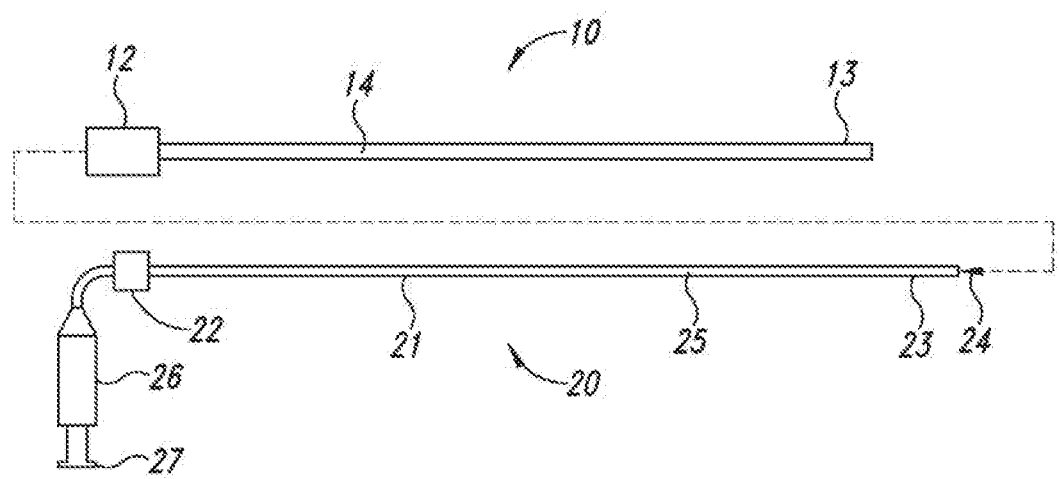
FIG. 1 is a side view of an intrabronchial neurotoxin delivery system of the present invention.

Referring to FIG. 1, apparatus for controlled delivery of neurotoxin to a target treatment area within a patient's bronchial airways to lessen the effects of asthma is described. Preferably, the apparatus comprises bronchoscope 10 and neurotoxin applicator assembly 20. Bronchoscope 10 has proximal end 12, distal end 13, and lumen 14. As is conventional, bronchoscope 10 also includes a light source for illuminating the interior of a patient's lung and optics, such as a miniature camera, that enables the physician to view the interior of the patient's lung. Alternatively, bronchoscope 10 may omit the light source and optics, and instead comprise an outer sheath. In this latter case, device 10 and neurotoxin applicator 20 would be observed using a separate conventional bronchoscope.

In accordance with the principles of the present invention, neurotoxin applicator assembly 20, of which various illustrative embodiments are described hereinbelow, enables the physician to selectively administer controlled doses of neurotoxin to or within selected treatment sites in the patient's lung. More specifically, neurotoxin applicator assembly 20 may be selectively advanced through lumen 14 of bronchoscope 10 to deliver a neurotoxin, such as botulinum toxin, serotype A, to a target treatment area.

Neurotoxin applicator assembly 20 includes shaft 21 coupled to at its proximal end to handle 22, distal end 23 having neurotoxin applicator 24, and lumen 25. Lumen 25 provides fluid communication between proximal end and handle 22 and applicator 24. Syringe 26 having plunger 27 is coupled to a port on proximal end 22. Syringe 26 is filled with neurotoxin in liquid form, and applies the neurotoxin to applicator 24 via lumen 25 when plunger 27 is actuated.

Handle 22 enables the physician to extend and retract applicator 24 from within lumen 14 of bronchoscope 10, and to manipulate distal end 23 of neurotoxin applicator assembly 20 under direct visual observation using the optics of bronchoscope 10. The neurotoxin applicator assembly preferably remains retracted within lumen 14 of the bronchoscope during insertion of the catheter into the patient's bronchial airways, and is deployed once the applicator is in a desired position. Alternatively, applicator 20 may be housed inside of a retaining sheath, and both units can be advanced through lumen 14 together.

Figure 2:
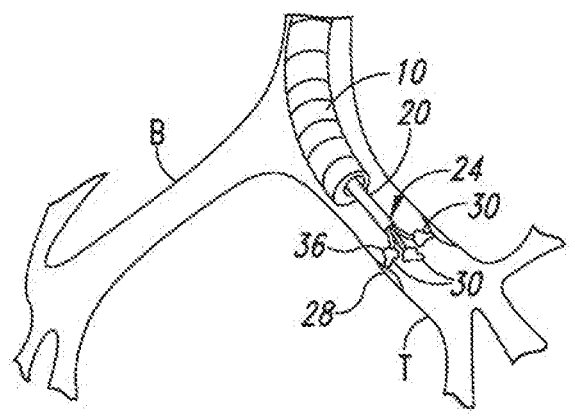
FIG. 2 is a perspective view of an illustrative embodiment of a neurotoxin applicator assembly of the present invention.

Referring now to FIGS. 2-3, a first illustrative embodiment of applicator 24 of neurotoxin applicator assembly 20 constructed in accordance with the principles of the present invention is described. Applicator 241 comprises needle assembly 28 having at least one needle 30 with lumen 31 in fluid communication with lumen 25. The needles are configured to penetrate the airway epithelium and directly inject small amounts of neurotoxin from the syringe into the collagenous and smooth muscle layers of bronchial wall B.

Figure 3A:
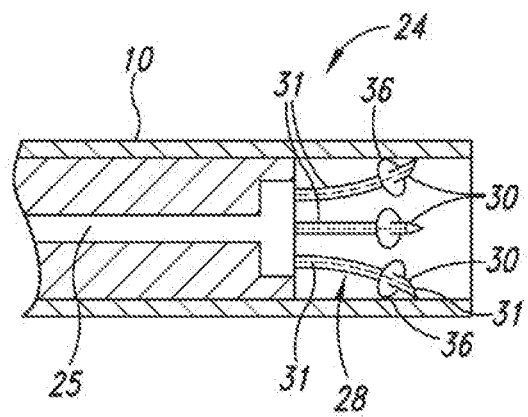
FIGS. 3A and 3B are cross-sectional views of the neurotoxin applicator assembly of FIG. 2 in retracted 30 and extended positions, respectively.
Figure 3B:
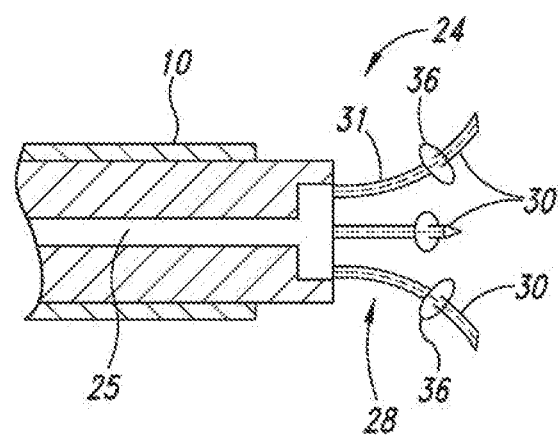

In FIG. 3A, needle assembly 28 is depicted 10 retracted with lumen 14 of bronchoscope 10. Alternatively, device 10 may comprise an outer sheath that is dimensioned to be slidably accept neurotoxin applicator assembly 20, and which is selectively retractable to expose needle assembly 28. In a further embodiment, a retaining sheath housed within lumen 14 and covering applicator 20 is selectably retractable to expose needle assembly 28. As depicted in FIG. 3B, needles 30 comprise a material capable of retaining a preformed shape, such as nickel-titanium, and are preformed to deflect radially outward when extended beyond distal end 13 of bronchoscope 10 (or the distal end of the outer sheath, if present). Each needle 30 optionally includes hilt 36 disposed a pre-selected distance from the distal end of the needle to control the depth of penetration of the needle tip into the bronchial wall.

When needle assembly 30 is deployed, as illustrated in FIGS. 2 and 3B, needles 30 penetrate target treatment area T of bronchial wall B so that neurotoxin may be injected in the bronchial wall. A controller (not shown) or a syringe 26 may include graduations that enable the physician to inject a pre-determined amount of neurotoxin at each target treatment area.

Figure 4:
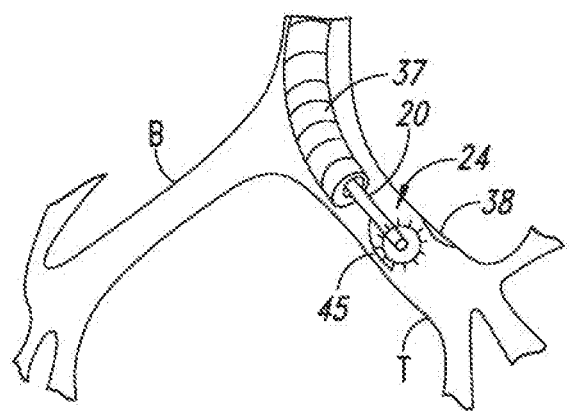
FIG. 4 is a perspective view of an alternative embodiment of a neurotoxin applicator assembly of the present invention.

Referring now to FIGS. 4 and 5, an alternative embodiment of applicator 24 of neurotoxin applicator assembly 20 is described. Applicator 24 in this embodiment comprises rotating needle assembly 38, including wheel 39 mounted to rotate about hub 40. While wheel 39 illustratively is round, it alternatively may comprise an ellipse or hexagon or other polygonal shape. Plurality of needles 41 is disposed around the circumference of the wheel, each needle 41 having lumen 42 in fluid communication with lumen 25 via a passageway in hub 40. Optional fender 45 protects a portion of the bronchial wall substantially opposite the target treatment area.

Figure 5A:
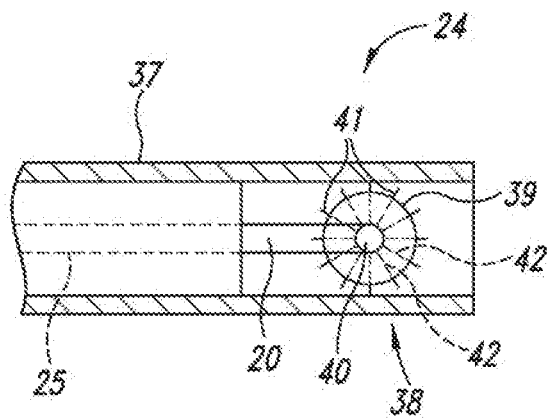
FIGS. 5A and 5B are partial cross-sectional views of the neurotoxin applicator assembly of FIG. 4 in retracted and extended positions, respectively.
Figure 5B:
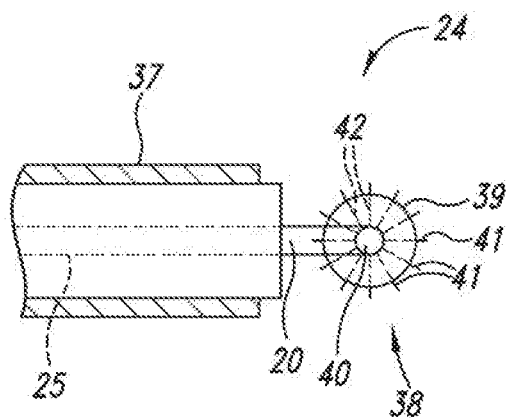

In FIG. 5A, rotating needle assembly 38 is shown retracted within outer sheath 37. Outer sheath 37 is dimensioned to fit within lumen 14 of bronchoscope 10, and may be selectively retracted to expose rotating needle assembly 38. Alternatively, rotating needle assembly 38 extends through lumen 14 and past the tip of bronchoscope 10. In this embodiment, the wheel is covered by a retractable protection sheath which covers the wheel during insertion of, the system. In FIGS. 4 and 5B, rotating needle assembly 38 is shown in the extended position. When so deployed, wheel 39 may be rolled across target treatment area T, so that as the wheel rotates needles 41 alternately penetrate and inject neurotoxin into bronchial wall B.

Suitable needles materials for needle assembly 28 of FIGS. 2-3 and rotating needle assembly 38 of FIGS. 4-5 include shape memory alloys such as nickel titanium alloys and spring tempered stainless steel alloys. Advantageously, either needle assembly permits direct injection of neurotoxin into the bronchial wall. This prevents the cilial transport system from trapping the neurotoxin and transporting it to other regions of the respiratory system, e.g., the oropharynx, where potentially unintended targets may be exposed to the neurotoxin, and prevents accidental exhalation of aerosolized neurotoxin.

Referring now to FIGS. 6A-C and 7, another alternative embodiment of applicator 24 of the neurotoxin applicator assembly of the present invention is described. Applicator 24 of FIGS. 6-7 comprises a needle-less injection assembly 46, which uses pressurized injection to deliver neurotoxin from a proximal controller 26' to target treatment area T. Advantageously, the needle-less injection assembly 46 allows controlled introduction of neurotoxin across the airway epithelium without the potential complications of introducing needles proximate to the delicate bronchial tissues, and may allow a lower profile system.

Needle-less injection assembly 46 comprises shaft 47 including at least one port 48 in fluid communication with lumen 25. Inflatable balloon 49 optionally may be coupled to shaft 47, and used to position the shaft adjacent target treatment area T. Balloon 49 is inflated with a fluid introduced through a lumen of shaft 47. When the shaft is aligned with the target treatment area, pulses of pressurized gas may be employed to inject predetermined amounts of neurotoxin across the airway wall and into the collagenous and smooth muscle layers.

Figure 6A:
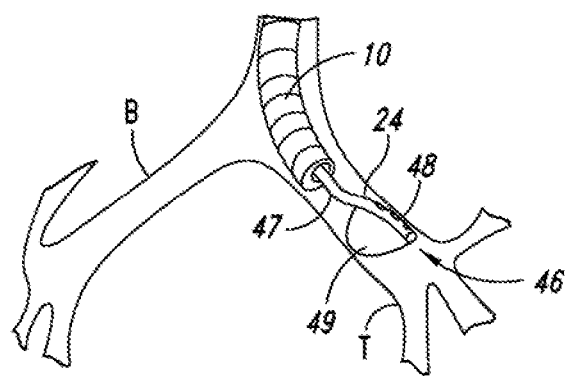
FIGS. 6A-6C are perspective view of other alternative embodiments of a neurotoxin applicator assembly of the present invention.
Figure 6B:
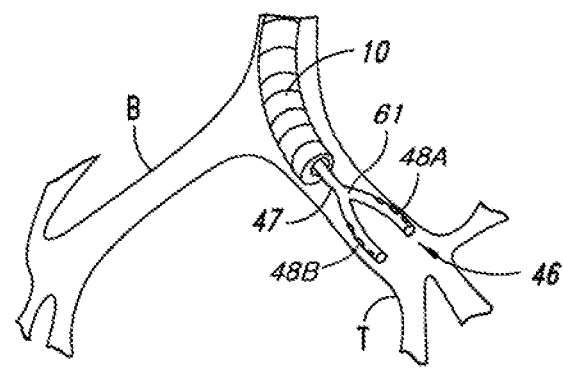
Figure 6C:
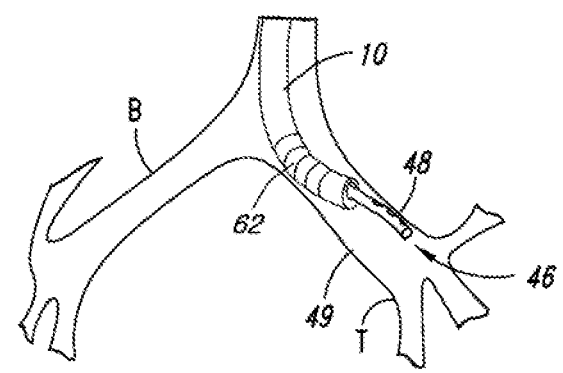
Figure 7A:
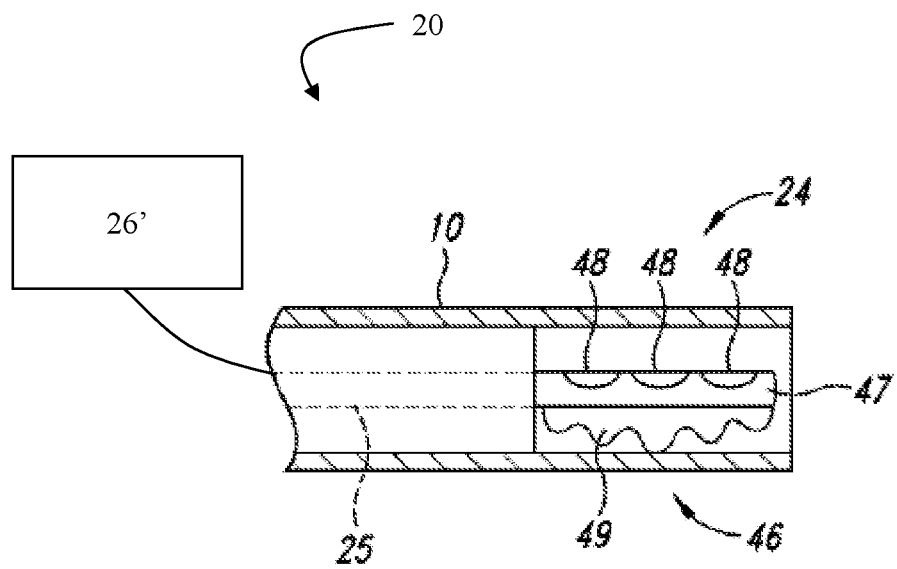
FIGS. 7A and 7B are partial cross-sectional views of the neurotoxin applicator assembly of FIG. 6 in retracted and extended positions, respectively.
Figure 7B:
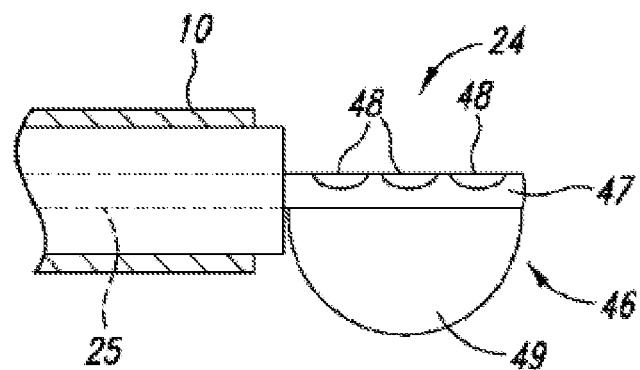

In FIG. 7A, needle-less injection assembly 46, with balloon 49 deflated, is depicted housed within the lumen 14 of bronchoscope 10 (or a separate outer sheath). FIGS. 6A and 7B depict needle-less injection assembly 46 with balloon 49 inflated to place ports 48 in apposition to target treatment area T. Once the physician has confirmed placement of needle-less injection assembly 46, e.g., by visualization using the optics of bronchoscope 10, fluoroscopy or other suitable means, a controller 26' attached to the proximal end of neurotoxin applicator assembly 20 (instead of syringe 26), may be activated to deliver the desired doses of neurotoxin to the bronchial wall. As an alternative to the balloon 49, as depicted in FIG. 6B, the assembly, may have two or more needle-less injectors 48A, 48B arranged to position against opposite walls of the bronchial passage. For instance, they might be spring loaded 61 to expand the sections away from the midline and contact the bronchial wall. As a further alternative, as depicted in FIG. 6C, the shaft of the assembly may be pre-curved or actively curved with an activation mechanism 62 to urge the injector against the wall of the bronchial passage.

Figure 8:
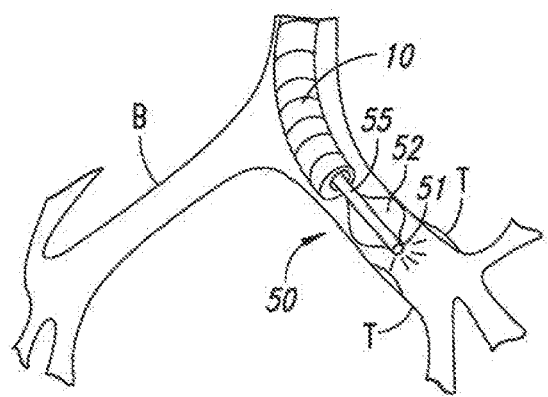
FIG. 8 is a perspective view of a yet further alternative embodiment of a neurotoxin applicator assembly of the present invention.
Figure 9A:
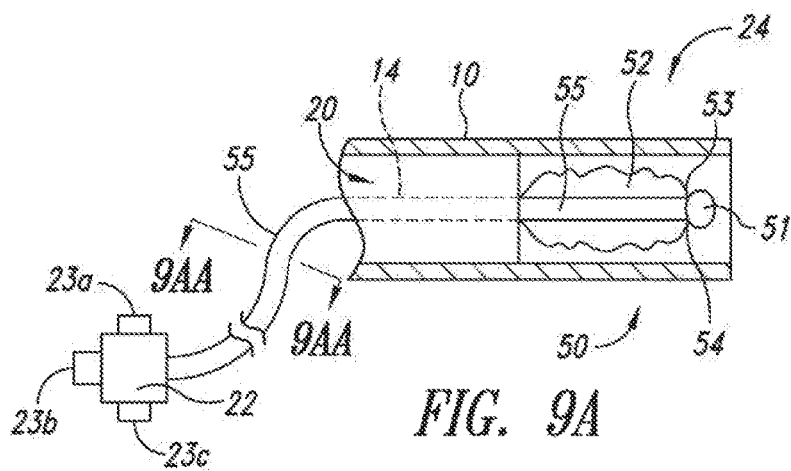
FIGS. 9A and 9B are partial cross-sectional views of the neurotoxin applicator assembly of FIG. 8 in retracted and extended positions, respectively.
Figure 9A:
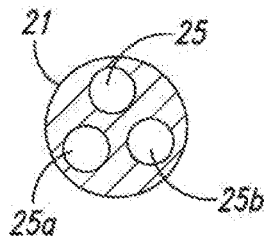

With respect to FIGS. 8 and 9, a yet further alternative embodiment of applicator 24 of the neurotoxin applicator assembly constructed in accordance with the present invention is described. Applicator 24 comprises nebulizer assembly 50 having shaft 55 with atomizer 51 disposed at its distal end and in fluid communication with central lumen 25.

Atomizer 51 converts the liquid neurotoxin from the syringe into a fine spray or mist. Particle size of the mist can be controlled through nebulizer head design or by varying injection pressure in order to control the depth of penetration of the mist into the target segment.

Nebulizer assembly 50 may also include optional inflatable balloon 52 disposed on shaft 55 proximal of atomizer 51. Selective inflation of balloon 52 allows positioning of atomizer 51 so that aerosolized neurotoxin may be directly sprayed onto target treatment area T. Balloon 52 also acts to isolate the treatment area from the rest of the lung, preventing reflux of mist into unintended areas. As for the embodiment of FIGS. 6-7, balloon 52' may be inflated using a fluid introduced through an auxiliary lumen in shaft 55.

Figure 9B:
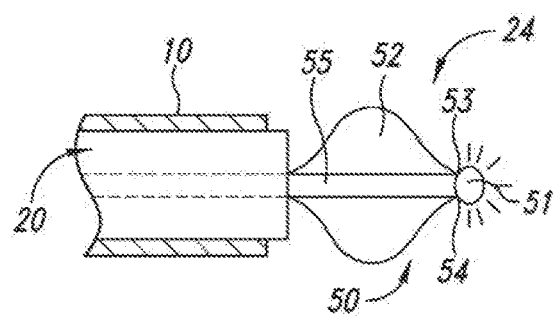

In FIG. 9A, the nebulizer assembly, including deflated balloon 52, is disposed within lumen 14 of bronchoscope 10, or alternatively, in an outer sheath (not shown) that is slidably received in lumen 14. Alternatively, the nebulizer assembly 50 may be inserted within a separate delivery sheath (not shown), with the bronchoscope 10 inserted separately. In FIGS. 8 and 9B, nebulizer assembly 50 is depicted deployed from lumen 14 (or the outer sheath, if present), with balloon 52 on shaft 55 inflated. Advantageously, nebulizer assembly 50 can be dimensioned to access very small bronchial passageways, and also may be used to deliver neurotoxin to upstream regions of the lung.

Still referring to FIGS. 9A and 9B, shaft 55 which carries balloon 52 may optionally also include an additional auxiliary lumen or lumens 25a, 25b (FIG. 9AA) coupled to inlet port 53 and outlet port 54 disposed between the balloon 52 and the atomizer 51. Lumen 25 provides for medicine delivery as in previous embodiments. Inlet port 53 allows the introduction of gas (such as fresh air) near the target treatment area, while outlet port 54 allows air or gas mixed with atomized neurotoxin to be removed. Inlet and outlet ports 53 and 54 therefore provide a ventilation system that shields tissue adjacent and proximal to target treatment area T from being inadvertently exposed to the atomized neurotoxin. Inlet and outlet ports 53 and 54 further serve to either actively inflate and deflate the isolated segment, or simply to normalize pressure within the lung near the target treatment area. The lumens 25, 25a, and 25b may be connected to the neurotoxin source, gas source, and an aspiration source via ports 23a, 23b, and 23c in handle 22. A control unit may be connected to the proximal outlets of ports 53 and 54 to control the introduction and removal of gases from the lung without allowing escape of atomized neurotoxin to the environment or patient.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A delivery device for delivering a pressurized treatment fluid to a target treatment area of a wall of an airway to treat a bronchial condition, the target treatment area extending only a portion of a circumference of the airway, the delivery device comprising:
   a shaft having a proximal end including an inlet port, a distal end and a lumen extending between the inlet port and the distal end;
   a needle-less injection assembly coupled to the distal end of the shaft on a first side of the shaft, and comprising at least one fluid injector in fluid communication with the lumen of the shaft; and
   a deflection mechanism disposed on a side of the shaft opposite the needle-less injection assembly, the deflection mechanism being configured to align the shaft with the target treatment area and urge the shaft and the at least one fluid injector adjacent to and in contact with the wall of the airway at a first contact area radially inward from the target treatment area by contacting the wall of the airway at a second contact area, the second contact area being opposite the airway from the first contact area, wherein the deflection mechanism is configured to contact the second contact area and not the first contact area, and
   wherein the at least one fluid injector is configured to directly inject the pressurized treatment fluid from the lumen across an epithelium of the wall of the airway at the first contact area and to the target treatment area while the at least one fluid injector is in contact with the wall of the airway to alter the target treatment area so as to treat the bronchial condition.

2. The delivery device of claim 1, wherein the deflection mechanism is an inflatable balloon.

3. The delivery device of claim 1, wherein the at least one fluid injector comprises at least one port configured to be placed in apposition to the target treatment area and to deliver a pressurized gas across the epithelium and to the target treatment area.

4. The delivery device of claim 1, wherein the needle-less injection assembly comprises a plurality of needle-less injectors arranged along the shaft so as to be placed in apposition to the wall of the airway in different locations along the airway at the first contact area.

5. The delivery device of claim 1, wherein the shaft is either pre-curved or actively curved with an activation mechanism to urge the at least one fluid injector adjacent to or against the wall of the airway at the first contact area.

6. The delivery device of claim 1, wherein the pressurized treatment fluid comprises a neurotoxin.

7. A system comprising the delivery device of claim 1, further comprising a bronchoscope having proximal and distal ends, a lumen extending therebetween, wherein the shaft is dimensioned to slidably pass through the lumen of the bronchoscope.

8. A system comprising the delivery device of claim 1, further comprising a controller coupled to the proximal end of the shaft, and configured to deliver a desired dose of the pressurized treatment fluid to the target treatment area.

* * * * *